(12) United States Patent
Touge et al.

(10) Patent No.: US 9,217,005 B2
(45) Date of Patent: Dec. 22, 2015

(54) RUTHENIUM-DIAMINE COMPLEXES AND METHOD FOR PRODUCING OPTICALLY ACTIVE COMPOUNDS

(75) Inventors: Taichiro Touge, Hiratsuka (JP); Hideki Nara, Hiratsuka (JP); Tomohiko Hakamada, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 59 days.

(21) Appl. No.: 13/819,188

(22) PCT Filed: Jun. 17, 2011

(86) PCT No.: PCT/JP2011/064490
§ 371 (c)(1),
(2), (4) Date: Feb. 26, 2013

(87) PCT Pub. No.: WO2012/026201
PCT Pub. Date: Mar. 1, 2012

(65) Prior Publication Data
US 2013/0158276 A1    Jun. 20, 2013

(30) Foreign Application Priority Data

Aug. 26, 2010 (JP) ................................. 2010-189738

(51) Int. Cl.
| | | |
|---|---|---|
| *C07F 15/00* | (2006.01) | |
| *C07C 29/143* | (2006.01) | |
| *C07C 209/52* | (2006.01) | |
| *C07D 311/22* | (2006.01) | |
| *C07F 19/00* | (2006.01) | |
| *C07D 307/42* | (2006.01) | |
| *C07C 253/30* | (2006.01) | |
| *B01J 31/18* | (2006.01) | |
| *B01J 31/22* | (2006.01) | |

(52) U.S. Cl.
CPC ......... *C07F 15/0046* (2013.01); *B01J 31/1805* (2013.01); *B01J 31/2295* (2013.01); *C07C 29/143* (2013.01); *C07C 209/52* (2013.01); *C07C 253/30* (2013.01); *C07D 307/42* (2013.01); *C07D 311/22* (2013.01); *C07F 19/00* (2013.01); *B01J 2231/326* (2013.01); *B01J 2231/643* (2013.01); *B01J 2231/646* (2013.01); *B01J 2531/0208* (2013.01); *B01J 2531/821* (2013.01); *B01J 2540/32* (2013.01); *H01L 2924/0002* (2013.01)

(58) Field of Classification Search
None
See application file for complete search history.

(56) References Cited

FOREIGN PATENT DOCUMENTS

WO    WO 2010/106364 A1 *    9/2010    ............... B01J 23/46

OTHER PUBLICATIONS

Mohri, et al., "Notification Concerning Transmittal of International Preliminary Report on Patentability (Chapter I of the Patent Cooperation Treaty)", Patent Cooperation Treaty, International Application No. PCT/JP2011/064490, mailed Mar. 7, 2013, The International Bureau of WIPO, Geneva, Switzerland, 5 pages.
Zassinovich et al., "Asymmetric Hydrogen Transfer reactions Promoted by Homogeneous Transition metal Catalysts", Chem Rev. (1992) p. 1051-1069.
Hashiguchi et al., "Asymmetric transfer hydrogenation of Aromatic Ketones Catalyzed by Chiral Ruthenium (II) Complexes", J. Am. Chem. Soc. 117 (1995) p. 7562-7563.
Fujji et al., "Ruthenium (II)-Catalyzed Asymmetric Transfer Hydrogenation of Ketones Using a formic Acid-Triethylamine Mixture", J. Am. Chem. Soc. 118 (1996) p. 2521-2522.
Uematsu et al.,"Asymmetirc transfer Hydrogenation of Imines", J. Am. Chem. Soc. 118 (1996) p. 4916-4917.

(Continued)

*Primary Examiner* — Yun Qian
(74) *Attorney, Agent, or Firm* — Mintz Levin Cohn Ferris Glovsky and Popeo, P.C.; Peter F. Corless; Christopher R. Cowles

(57) ABSTRACT

Provided is a catalyst for asymmetric reduction, which can be produced by a convenient and safe production method, has a strong catalytic activity, and has excellent stereoselectivity. The present invention relates to a ruthenium complex represented by the following formula (1): wherein $R^1$ represents an alkyl group or the like; Y represents a hydrogen atom; X represents a halogen atom or the like; j and k each represent 0 or 1; $R^2$ and $R^3$ each represent an alkyl group or the like; $R^{11}$ to $R^{19}$ each represent a hydrogen atom, an alkyl group or the like; Z represents oxygen or sulfur; $n_1$ represents 1 or 2; and $n_2$ represents an integer from 1 to 3, a method for producing the ruthenium complex, a catalyst for asymmetric reduction formed from the ruthenium complex, and methods for selectively producing an optically active alcohol and an optically active amine using the catalyst for asymmetric reduction.

(1)

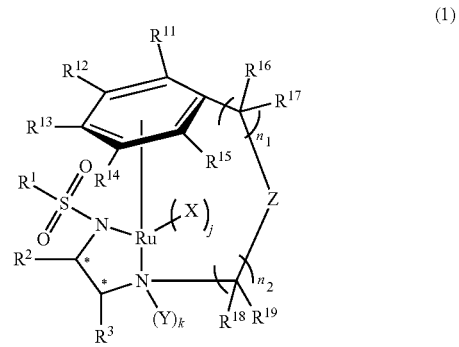

16 Claims, No Drawings

(56) References Cited

OTHER PUBLICATIONS

Hayes et al., "A Class of Ruthenium (III) Catalyst for Asymmetric Transfers Hydrogenations of Ketones", J. Am. Chem. Soc. 127 (2005) p. 7318-7319.

Morris et al., "The "Reverse-Tethered" Ruthenium (II) Catalyst for Asymmetric Transfer Hydrogenation: Further Applications", J. Org. Chem. 71 (2006) p. 7035-7044.

Cheung et al., "The use of a [4+2] cycloaddition reaction for the preparation of a series of 'tethered' Ru(II)-diamine and aminoalcohol complexes", Org. Biomol. Chem. 5 (2007) p. 1093-1103.

Cheung et al., "An Investigation into the Tether Length and Substitution Pattern of Arene-Substitution Complexes for Asymmetric Transfer Hydrogenation of Ketones", Org. Lett. 9 (2007) p. 4659-4662.

Martins et al., "Further 'tethered' Ru(II) catalyst for asymmetric transfer hydrogenation (ATH) of Ketones; the use of a benzylic linker and a cyclohexyldiamine ligand", J. Organometallic. Chem. 693 (2008) p. 3527-3532.

Cheung et al., "Kinetic and structural studies on 'tethered' Ru(II) arene ketone reduction catalysts", Dalton. Trans. 39 (2010) p. 1395-1402.

\* cited by examiner

RUTHENIUM-DIAMINE COMPLEXES AND METHOD FOR PRODUCING OPTICALLY ACTIVE COMPOUNDS

RELATED APPLICATIONS

This application is the U.S. national phase, pursuant to 35 U.S.C. §371, of PCT international application PCT/JP2011/064490, filed Jun. 17, 2011, designating the United States and published on Mar. 1, 2012 as WO 2012/026201 A1, which claims priority to Japanese application 2010-189738, filed Aug. 26, 2010. The entire contents of the aforementioned patent applications are incorporated herein by this reference.

TECHNICAL FIELD

The present invention relates to novel ruthenium-diamine complexes, and methods for selectively producing an optically active alcohol and an optically active amine, which are important as precursors for the syntheses of pharmaceutical products and functional materials, by using the complexes as catalysts.

BACKGROUND ART

Numerous asymmetric reactions including asymmetric reduction have been developed, and there have been many reports on asymmetric reactions which use an asymmetric metal complex having an optically active phosphine ligand as a catalyst that is used in those asymmetric reactions. On the other hand, it has been frequently reported that, for example, a complex in which an optically active nitrogen compound is coordinated to a transition metal such as ruthenium, rhodium or iridium, has excellent performance as a catalyst for asymmetric synthesis reactions. Thus, a wide variety of optically active nitrogen compounds have been hitherto developed in order to enhance the performance of this catalyst (Non-Patent Literatures 1, 2, 3 and 4).

Among others, M. Wills et al. have reported complexes in which a diamine moiety and an aromatic compound (arene) portion coordinating a ruthenium complex are linked via a carbon chain, and these complexes are known to exhibit a higher activity as compared with conventional catalysts (Non-Patent Literatures 5, 6, 7, 8, 9 and 10).

CITATION LIST

Non Patent Literature

NPL 1: Chem Rev. (1992) p. 1051
NPL 2: J. Am. Chem. Soc. 117 (1995) p. 7562
NPL 3: J. Am. Chem. Soc. 118 (1996) p. 2521
NPL 4: J. Am. Chem. Soc. 118 (1996) p. 4916
NPL 5: J. Am. Chem. Soc. 127 (2005) p. 7318
NPL 6: J. Org. Chem. 71 (2006) p. 7035
NPL 7: Org. Biomol. Chem. 5 (2007) p. 1093
NPL 8: Org. Lett. 9 (2007) p. 4659
NPL 9: J. Organometallic. Chem. 693 (2008) p. 3527
NPL 10: Dalton. Trans. 39 (2010) p. 1395

SUMMARY OF INVENTION

Technical Problem

However, in the conventional methods using these complexes, the catalytic activity and the enantiomeric excess may be insufficient depending on the subject reaction or the reaction substrate, and development of new complexes is desired. Furthermore, even the methods for synthesizing those complexes are complicated, or are of low yield, so that many of the methods cause problems in industrial applications and the like.

The present invention was made to solve such problems.

Solution to Problem

In order to solve the problems described above, the inventors of the present invention paid attention to the chain-like moiety that links the aromatic compound (arene) portion and the diamine moiety that are coordinated to a ruthenium complex having an optically active diamine, and the inventors found that when the chain-like moiety is constructed as a chain-like moiety having a heteroatom, there is obtained a novel ruthenium-diamine complex which has a high catalytic activity and a satisfactory enantiomeric excess, and which can be produced by a simple method and is appropriate for industrial use.

That is, the present invention relates to a ruthenium complex represented by the formula (1) shown below, a method for producing the ruthenium complex, a catalyst for asymmetric reduction formed from the ruthenium complex, and methods for selectively producing an optically active alcohol and an optically active amine using the catalyst for asymmetric reduction.

The present invention includes the following matters.

[1] A ruthenium complex represented by the following formula (1):

[Chem. 1]

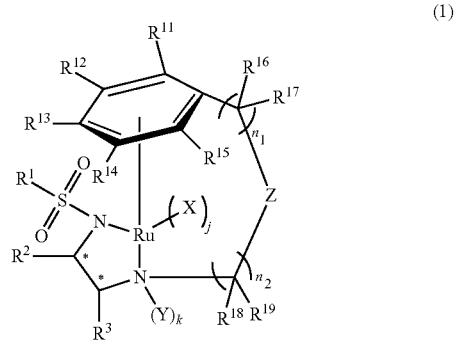

(1)

wherein symbol * represents an asymmetric carbon atom;

$R^1$ represents an alkyl group having 1 to 10 carbon atoms; a halogenated alkyl group having 1 to 10 carbon atoms; 10-camphoryl group; an amino group which may be substituted with one or two alkyl group having 1 to 10 carbon atoms; an aryl group which may be substituted with an alkyl group having 1 to 10 carbon atoms, a halogenated alkyl group having 1 to 10 carbon atoms, a halogen atom, a cyano group (—CN), an amino group, an alkylated amino group (—NR$^{20}$R$^{21}$), a five or six membered cyclic amino group, an acylated amino group (—NH—CO—R$^{20}$), a hydroxyl group, an alkoxy group (—OR$^{20}$), an acyl group (—CO—R$^{20}$), a carboxyl group, an alkoxycarbonyl group (—COOR$^{20}$), a phenoxy carbonyl group, a mercapto group, an alkylthio group (—SR$^{20}$), a silyl group (—SiR$^{20}$R$^{21}$R$^{22}$), or a nitro group (—NO$_2$); R$^{20}$, R$^{21}$ and R$^{22}$ each independently represent a hydrogen atom, an alkyl group having 1 to 10 carbon atoms or a cycloalkyl group having 3 to 10 carbon atoms;

Y represents a hydrogen atom;

X represents a trifluoromethanesulfonyloxy group, a p-toluenesulfonyloxy group, a methanesulfonyloxy group, a benzenesulfonyloxy group, a hydrogen atom, or a halogen atom;

j and k each represent 0 or 1, but j+k is not 1;

$R^2$ and $R^3$ each independently represent a hydrogen atom; an alkyl group having 1 to 10 carbon atoms; a phenyl group which may be substituted with an alkyl group having 1 to 10 carbon atoms, an alkoxy group having 1 to 10 carbon atoms, or a halogen atom; or a cycloalkyl group having 3 to 8 carbon atoms, or $R^2$ and $R^3$ may be joined together to form a ring;

$R^{11}$, $R^{12}$, $R^{13}$, $R^{14}$ and $R^{15}$ each independently represent a hydrogen atom, an alkyl group having 1 to 10 carbon atoms, or an alkoxy group having 1 to 10 carbon atoms;

$R^{16}$, $R^{17}$, $R^{18}$ and $R^{19}$ each independently represent a hydrogen atom, a hydroxyl group, an alkyl group having 1 to 10 carbon atoms, or an alkoxy group having 1 to 10 carbon atoms, or $R^{16}$ and $R^{17}$ with the carbon atom which is substituted with $R^{16}$ and $R^{17}$, and/or $R^{18}$ and $R^{19}$ with the carbon atom which is substituted with $R^{18}$ and $R^{19}$ may form a carbonyl group(s);

Z represents an oxygen atom or a sulfur atom; and $n_1$ represents 1 or 2, and $n_2$ represents an integer from 1 to 3.

[2] A ruthenium complex represented by the following formula (2):

[Chem. 2]

(2)

wherein symbol * represents an asymmetric carbon atom;

$R^1$ represents an alkyl group having 1 to 10 carbon atoms; a halogenated alkyl group having 1 to 10 carbon atoms; 10-camphoryl group; an amino group which may be substituted with one or two alkyl group having 1 to 10 carbon atoms; an aryl group which may be substituted with an alkyl group having 1 to 10 carbon atoms, a halogenated alkyl group having 1 to 10 carbon atoms, a halogen atom, a cyano group (—CN), an amino group, an alkylated amino group (—$NR^{20}R^{21}$), a five or six membered cyclic amino group, an acylated amino group (—NH—CO—$R^{20}$), a hydroxyl group, an alkoxy group (—$OR^{20}$), an acyl group (—CO—$R^{20}$), a carboxyl group, an alkoxycarbonyl group (—$COOR^{20}$), a phenoxy carbonyl group, a mercapto group, an alkylthio group (—$SR^{20}$), a silyl group (—$SiR^{20}R^{21}R^{22}$), or a nitro group (—$NO_2$); $R^{20}$, $R^{21}$ and $R^{22}$ each independently represent a hydrogen atom, an alkyl group having 1 to 10 carbon atoms or a cycloalkyl group having 3 to 10 carbon atoms;

Y represents a hydrogen atom;

$R^2$ and $R^3$ each independently represent a hydrogen atom; an alkyl group having 1 to 10 carbon atoms; a phenyl group which may be substituted with an alkyl group having 1 to 10 carbon atoms, an alkoxy group having 1 to 10 carbon atoms, or a halogen atom; or a cycloalkyl group having 3 to 8 carbon atoms, or $R^2$ and $R^3$ may be joined together to form a ring;

$R^{11}$, $R^{12}$, $R^{13}$, $R^{14}$ and $R^{15}$ is each independently represent a hydrogen atom, an alkyl group having 1 to 10 carbon atoms, or an alkoxy group having 1 to 10 carbon atoms;

$R^{16}$, $R^{17}$, $R^{18}$ and $R^{19}$ each independently represent a hydrogen atom, a hydroxyl group, an alkyl group having 1 to 10 carbon atoms, or an alkoxy group having 1 to 10 carbon atoms, or $R^{16}$ and $R^{17}$ with the carbon atom which is substituted with $R^{16}$ and $R^{17}$, and/or $R^{18}$ and $R^{19}$ with the carbon atom which is substituted with $R^{18}$ and $R^{19}$ may form a carbonyl group(s);

Z represents an oxygen atom or a sulfur atom;

Q represents a counter anion; and $n_1$ represents 1 or 2, and $n_2$ represents an integer from 1 to 3.

[3] A ruthenium complex represented by the following formula (3):

[Chem. 3]

(3)

wherein symbol * represents an asymmetric carbon atom;

$R^1$ represents an alkyl group having 1 to 10 carbon atoms; a halogenated alkyl group having 1 to 10 carbon atoms; 10-camphoryl group; an amino group which may be substituted with one or two alkyl group having 1 to 10 carbon atoms; an aryl group which may be substituted with an alkyl group having 1 to 10 carbon atoms, a halogenated alkyl group having 1 to 10 carbon atoms, a halogen atom, a cyano group (—CN), an amino group, an allkylated amino group (—$NR^{20}NR^{21}$), a five or six membered cyclic amino group, an acylated amino group (—NH—CO—$R^{20}$), a hydroxyl group, an alkoxy group (—$OR^{20}$), an acyl group (—CO—$R^{20}$), a carboxyl group, an alkoxycarbonyl group (—$COOR^{20}$), a phenoxy carbonyl group, a mercapto group, an alkylthio group (—$SR^{20}$), a silyl group (—$SiR^{20}R^{21}R^{22}$), or a nitro group (—$NO_2$); $R^{20}$, $R^{21}$ and $R^{22}$ each independently represent a hydrogen atom, an alkyl group having 1 to 10 carbon atoms or a cycloalkyl group having 3 to 10 carbon atoms;

Y represents a hydrogen atom;

$R^2$ and $R^3$ each independently represent a hydrogen atom; an alkyl group having 1 to 10 carbon atoms; a phenyl group which may be substituted with an alkyl group having 1 to 10 carbon atoms, an alkoxy group having 1 to 10 carbon atoms, or a halogen atom; or a cycloalkyl group having 3 to 8 carbon atoms, or $R^2$ and $R^3$ may be joined together to form a ring;

$R^{11}$, $R^{12}$, $R^{13}$, $R^{14}$ and $R^{15}$ each independently represent a hydrogen atom, an alkyl group having 1 to 10 carbon atoms, or an alkoxy group having 1 to 10 carbon atoms;

$R^{16}$, $R^{17}$, $R^{18}$ and $R^{19}$ each independently represent a hydrogen atom, a hydroxyl group, an alkyl group having 1 to 10 carbon atoms, or an alkoxy group having 1 to 10 carbon atoms, or $R^{16}$ and $R^{17}$ with the carbon atom which is substituted with $R^{16}$ and $R^{17}$, and/or $R^{18}$ and $R^{19}$ with the carbon atom which is substituted with $R^{18}$ and $R^{19}$ may form a carbonyl group(s);

Z represents an oxygen atom or a sulfur atom;

V represents a halogen atom; and $n_1$ represents 1 or 2, and $n_2$ represents an integer from 1 to 3.

[4] A method for producing a reduction product by reducing an organic compound in the presence of the ruthenium complex as set forth in any one of [1] to [3] and a hydrogen donor.

[5] A method for producing an optically active alcohol, the method comprising reducing a carbonyl group of a carbonyl compound in the presence of the ruthenium complex according to any one of [1] to [3] and a hydrogen donor.

[6] A method for producing an optically active amine, the method comprising reducing an imino group of an imine compound in the presence of the ruthenium complex according to any one of [1] to [3] and a hydrogen donor.

[7] The method according to any one of [4] to [6], wherein the hydrogen donor is selected from formic acid, a formic acid alkali metal salt, and an alcohol having a hydrogen atom on the α-position carbon atom substituted with a hydroxyl group.

[8] The method according to any one of [4] to [6], wherein the hydrogen donor is hydrogen.

[9] A catalyst for reduction, comprising the ruthenium complex according to any one of [1] to [3].

[10] The catalyst for reduction according to [9], wherein the catalyst for reduction is a catalyst for asymmetric reduction.

Advantageous Effects of Invention

The present invention is to provide a novel ruthenium-diamine complexes having a heteroatom introduced into the chain-like moiety that links the aromatic compound (arene) portion and the diamine moiety that are coordinated to ruthenium. The ruthenium-diamine complexes of the present invention have highly catalytic activities, can be used for the reduction of the portion of carbonyl group, imino group and ester group are useful as catalysts for various hydrogenation reactions. Also, the complexes of the present invention, in which the ligand is an optically active substance, are excellent in stereoselectivity and give high enantiomeric excess values. Conventional complexes, in which the arene portion and the diamine portion are linked via a carbon chain only, are highly active; however, the conventional complexes have problems that the methods for synthesis of the complexes are complicated; that the synthesis of the complexes utilizes the Birch reduction, by which the use of toxic ammonia gas or cryogenic apparatuses is unavoidable; that the Swern oxidation must be used, in which the stench odor of dimethyl sulfide that is produced as a side product, harmfulness of carbon monoxide, the necessity of cryogenic apparatuses, and the like cause a problem in the application of the oxidation process in an industrial scale; and that the complexes give low yield in some of the reactions. However, when a heteroatom is introduced into the chain-like moiety according to the present invention, a complex having a side chain that links an arene portion and a diamine portion can be synthesized more conveniently and efficiently by using an appropriate ruthenium-arene dimer and an appropriate diamine, and by performing a thioetherification or etherification reaction simultaneously with the formation of the complex.

Furthermore, the ruthenium complexes of the present invention having a heteroatom introduced into the chain-like moiety have higher catalytic activities as compared with the conventional complexes which do not have a heteroatom in the corresponding chain-like moiety, and in which the chain-like moiety is composed of a carbon chain only. When the ruthenium complexes of the present invention are used, target substances can be obtained with high optical purity and high yield by a hydrogen transfer reaction or a hydrogenation reaction. Particularly, the complexes of the present invention in which the ligand is an optically active substance are useful as catalysts for asymmetric reduction.

When the ruthenium-diamine complexes of the present invention are used, an optically active alcohol or an optically active amine, which are both useful as raw materials for pharmaceutical products and functional materials, can be selectively produced.

DESCRIPTION OF EMBODIMENTS

The ruthenium complexes of the present invention represented by the formulas (1), (2), and (3) are ruthenium complexes characterized in that an aromatic compound (arene) portion is coordinated to a ruthenium atom, and the chain-like moiety which links the aromatic compound (arene) portion and a diamine moiety has a heteroatom such as an oxygen atom or a sulfur atom introduced therein.

Furthermore, the ruthenium complexes represented by the formulas (1) and (2) are characterized in that two nitrogen atoms of a diamine ligand are bonded to a ruthenium atom via covalent bonding or coordination bonding, an aromatic compound (arene) portion that is bonded to the diamine also has a tridentate ligand which is coordinated to the ruthenium atom, and the chain-like moiety that links the aromatic compound (arene) portion and the diamine moiety has a heteroatom such as an oxygen atom or a sulfur atom introduced therein.

The symbol * in the formulas (1), (2) and (3) represents that the carbon atom to which the symbol * is attached may optionally become an asymmetric carbon atom. When the carbon atom becomes an asymmetric carbon atom, the resultant products may be optically active substances of the ruthenium complexes, may be mixtures of optically active substances, or may be racemates (including racemic compounds). In a preferred embodiment of the present invention, when these carbon atoms become asymmetric carbon atoms, the resultant products may be optically active substances of the ruthenium complexes.

Furthermore, the ruthenium complexes represented by the formula (2) is ruthenium complexes in the case where the Ru—X bond in the ruthenium complexes represented by the formula (1) become an ionic bond of $Ru^+$-$Q^-$.

The ruthenium complex represented by the formula (3) is a dimer interrupted by a halogen atom V, and is a complex in which an aromatic compound (arene) portion is coordinated to a ruthenium atom. The ruthenium complex represented by the formula (3) is a ruthenium complex which is not only useful as an intermediate in the production of a ruthenium complex represented by the formula (1) or (2), but also has an activity as a reducing catalyst per se.

In regard to the formulas (1), (2), and (3) of the present invention, the alkyl group having 1 to 10 carbon atoms represented by $R^1$ may be a linear or branched alkyl group having 1 to 10 carbon atoms, and preferably 1 to 5 carbon atoms. Specific examples of the alkyl group include a methyl group, an ethyl group, an n-propyl group, an isopropyl group, an n-butyl group, an isobutyl group, an s-butyl group, a t-butyl group, an n-pentyl group, an n-hexyl group, an n-heptyl group, an n-octyl group, an n-nonyl group, and an n-decyl group.

In regard to the formulas (1), (2), and (3) of the present invention, the halogenated alkyl group having 1 to 10 carbon atoms represented by $R^1$ is an alkyl group having 1 to 10 carbon atoms, in which a linear or branched alkyl group described above such as, for example, a methyl group, an ethyl group, an n-propyl group, an isopropyl group, an n-butyl group or an n-hexyl group, is substituted with one or more of halogen atoms such as a fluorine atom, a chlorine atom and a bromine atom. Examples the halogenated alkyl group include perfluoroalkyl groups such as a trifluoromethyl group, a pentafluoromethyl group, and a heptafluoropropyl group.

In regard to the formulas (1), (2), and (3) of the present invention, the aryl group of the aryl group which is optionally substituted with an alkyl group having 1 to 10 carbon atoms, a halogenated alkyl group having 1 to 10 carbon atoms, a halogen atom, a cyano group (—CN), an amino group, an alkylated amino group (—$NR^{20}R^{21}$), a five or six membered cyclic amino group, an acylated amino group (—NH—CO—$R^{20}$), a hydroxyl group, an alkoxy group (—$OR^{20}$), an acyl group (—CO—$R^{20}$), a carboxyl group, an alkoxycarbonyl group (—$COOR^{20}$), a phenoxy carbonyl group, a mercapto group, an alkylthio group (—$SR^{20}$), a silyl group (—$SiR^{20}R^{21}R^{22}$), or a nitro group (—$NO_2$), as represented by $R^1$, may be a monocyclic, polycyclic or fused-ring aryl group having 1 to 20 carbon atoms, and preferably 6 to 12 carbon atoms, such as a phenyl group or a naphthyl group. The alkyl group having 1 to 10 carbon atoms may be the same alkyl group as defined above. The halogenated alkyl group having 1 to 10 carbon atoms may be the same halogenated alkyl group as defined above, for example, a perfluoroakyl group. The halogen atom may be a fluorine atom, a chlorine atom or the like.

The alkylated amino group is represented by the formula —$NR^{20}R^{21}$, wherein $R^{20}$ and $R^{21}$ each independently represent a hydrogen atom, an alkyl group having 1 to 10 carbon atoms or cycloalkyl group having 3 to 10 carbon atoms. Examples of the alkylated amino group, include mono- or di-alkylamino groups such as N-methylamino, N,N-dimethylamino, N,N-diethylamino, N,N-diisopropylamino or N-cyclohexylamino groups, or the like.

The five- or six-membered cyclic amino group is a 5 or 6-membered saturated or unsaturated heterocyclic group having one or two basic nitrogen atoms. Examples of the five- or six-membered cyclic amino group include a pyrrolidino group, piperidino group or a morpholino group, or the like.

The acyl group is represented by the formula —CO—$R^{20}$, wherein $R^{20}$ represent a hydrogen atom, an alkyl group having 1 to 10 carbon atoms or cycloalkyl group having 3 to 10 carbon atoms. Examples of the acyl group, include formyl, acetyl, propionyl, butyryl, pivaloyl, pentanoyl or hexanoyl, or the like.

The acylated amino group is represented by the formula —NH—CO—$R^{20}$, wherein $R^{20}$ represent a hydrogen atom, an alkyl group having 1 to 10 carbon atoms or cycloalkyl group having 3 to 10 carbon atoms. Examples of the acylated amino group, include formylamino, acetylamino, propionylamino, pivaloylamino, pentanoylamino or hexanoylamino, or the like.

The alkoxy group is represented by the formula —$OR^{20}$, wherein $R^{20}$ represent a hydrogen atom, an alkyl group having 1 to 10 carbon atoms or cycloalkyl group having 3 to 10 carbon atoms, for example, methoxy, ethoxy, n-propoxy, isopropoxy, n-butoxy, s-butoxy, isobutoxy, t-butoxy, n-pentyloxy, 2-methylbutoxy, 3-methylbutoxy, 2,2-dimethylpropyloxy, n-hexyloxy, 2-methylpentyloxy, 3-methylpentyloxy, 4-methylpentyloxy, 5-methylpentyloxy or cyclohexyloxy groups, or the like.

The alkoxycarbonyl group is represented by the formula —$COOR^{20}$, wherein $R^{20}$ represent a hydrogen atom, an alkyl group having 1 to 10 carbon atoms or cycloalkyl group having 3 to 10 carbon atoms, for example, methoxycarbonyl, ethoxycarbonyl, n-propoxycarbonyl, isopropoxycarbonyl, n-butoxycarbonyl, t-butoxycarbonyl, pentyloxycarbonyl, hexyloxycarbonyl or 2-ethylhexyloxycarbonyl, or the like.

The alkylthio group is represented by the formula —$SR^{20}$, wherein $R^{20}$ represent a hydrogen atom, an alkyl group having 1 to 10 carbon atoms or cycloalkyl group having 3 to 10 carbon atoms, for example, methylthio, ethylthio, n-propylthio, isopropylthio, n-butylthio, s-butylthio, isobutylthio, t-butylthio, pentylthio, hexylthio or cyclohexylthio groups, or the like.

The silyl group is represented by the formula —$SiR^{20}R^{21}R^{22}$, wherein $R^{20}$, $R^{21}$ and $R^{22}$ each independently represent a hydrogen atom, an alkyl group having 1 to 10 carbon atoms or cycloalkyl group having 3 to 10 carbon atoms, for example, trimethylsilyl, triisopropylsilyl, t-butyldimethylsilyl, t-butyldiphenylsilyl or triphenylsilyl groups, or the like.

The cycloalkyl group having 3 to 10 carbon atoms is a monocyclic, polycyclic or fused-ring, and saturated or unsaturated 3 to 7-membered cycloalkyl group having 3 to 10 carbon atoms.

Examples of such an aryl group include a phenyl group, an o-, m- or p-tolyl group, an o-, m- or p-ethylphenyl group, an o-, m- or p-isopropylphenyl group, an o-, m- or p-t-butylphenyl group, a 2,4,6-trimethylphenyl group, a 3,5-xylyl group, a 2,4,6-triisopropylphenyl group, an o-, m- or p-trifluoromethylphenyl group, an o-, m- or p-fluorophenyl group, an o-, m- or p-chlorophenyl group, and a pentafluorophenyl group.

In regard to the formulas (1), (2), and (3) of the present invention, the alkyl group having 1 to 10 carbon atoms represented by $R^2$ and $R^3$ may be a linear or branched alkyl group having 1 to 10 carbon atoms, and preferably 1 to 5 carbon atoms. Specific examples of the alkyl group include a methyl group, an ethyl group, an n-propyl group, an isopropyl group, an n-butyl group, an isobutyl group, an s-butyl group, a t-butyl group, an n-pentyl group, an n-hexyl group, an n-heptyl group, an n-octyl group, an n-nonyl group, and an n-decyl group.

In regard to the formulas (1), (2), and (3) of the present invention, the alkyl group of the phenyl group which may be substituted with an alkyl group having 1 to 10 carbon atoms, an alkoxy group having 1 to 10 carbon atoms, or a halogen atom, as represented by $R^2$ and $R^3$, may be, for example, the same alkyl group as defined above. Examples of the halogen atom include a fluorine atom, a chlorine atom, and a bromine atom.

The alkoxy group having 1 to 10 carbon atoms may be a linear or branched alkoxy group having 1 to 10 carbon atoms, and preferably 1 to 5 carbon atoms. Specific examples of the alkoxy group include a methoxy group, an ethoxy group, an n-propoxy group, an isopropoxy group, an n-butoxy group, an isobutoxy group, an s-butoxy group, a t-butoxy group, an n-pentyloxy group, an n-hexyloxy group, an n-heptyloxy group, an n-octyloxy group, an n-nonyloxy group, and an n-decyloxy group.

In regard to the formulas (1), (2), and (3) of the present invention, the cycloalkyl group having 3 to 8 carbon atoms as represented by $R^2$ and $R^3$ may be a monocyclic, polycyclic or bridged cycloalkyl group having 3 to 8 carbon atoms, and preferably 5 to 8 carbon atoms. Specific examples of the cycloalkyl group include a cyclopropyl group, a cyclobutyl group, a cyclopentyl group, a cyclohexyl group, a cycloheptyl group, and a cyclooctyl group. These cycloalkyl groups may be substituted with an alkyl group such as a methyl group, an isopropyl group or a t-butyl group, or the like.

Furthermore, when $R^2$ and $R^3$ are joined together to form a ring, $R^2$ and $R^3$ are joined to form a linear or branched alkylene group having 2 to 10 carbon atoms, and preferably 3 to 10 carbon atoms, and the resulting alkylene group forms, together with adjacent carbon atoms, a 4- to 8-membered, and preferably 5- to 8-membered, cycloalkane ring. Preferred examples of the cycloalkane ring include a cyclopentane ring, a cyclohexane ring, and a cycloheptane ring, and these rings may each have an alkyl group such as a methyl group, an isopropyl group or a t-butyl group as a substituent.

In regard to the arene moiety represented by the formulas (1), (2), and (3) of the present invention, $R^{11}$, $R^{12}$, $R^{13}$, $R^{14}$ and $R^{15}$ each independently represent a hydrogen atom, an alkyl group having 1 to 10 carbon atoms, or an alkoxy group having 1 to 10 carbon atoms. The alkyl group may be the same alkyl group as defined above, and specific examples of the alkyl group include a methyl group, an ethyl group, an n-propyl group, an isopropyl group, an n-butyl group, an isobutyl group, an s-butyl group, a t-butyl group, an n-pentyl group, an n-hexyl group, an n-heptyl group, an n-octyl group, an n-nonyl group, and an n-decyl group.

The alkoxy group may be the same linear or branched alkoxy group as defined above, and specific examples of the alkoxy group include a methoxy group, an ethoxy group, an n-propoxy group, an isopropoxy group, an n-butoxy group, an isobutoxy group, an s-butoxy group, a t-butoxy group, an n-pentyloxy group, an n-hexyloxy group, an n-heptyloxy group, an n-octyloxy group, an n-nonyloxy group, and an n-decyloxy group.

$R^{16}$, $R^{17}$, $R^{18}$ and $R^{19}$ representing the substituents substituted on the carbon atoms of the chain-like moiety that links the arene portion and the diamine moiety represented by the formulas (1), (2), and (3), each independently represent a hydrogen atom, a hydroxyl group, an alkyl group having 1 to 10 carbon atoms, or an alkoxy group having 1 to 10 carbon atoms. The alkyl group may be the same alkyl group as defined above, and specific examples thereof include a methyl group, an ethyl group, an n-propyl group, an isopropyl group, an n-butyl group, an isobutyl group, an s-butyl group, a t-butyl group, an n-pentyl group, an n-hexyl group, an n-heptyl group, an n-octyl group, an n-nonyl group, and an n-decyl group.

The alkoxy group may be the same linear or branched alkoxy group as defined above, and specific examples of the alkoxy group include a methoxy group, an ethoxy group, an n-propoxy group, an isopropoxy group, an n-butoxy group, an isobutoxy group, an s-butoxy group, a t-butoxy group, an n-pentyloxy group, an n-hexyloxy group, an n-heptyloxy group, an n-octyloxy group, an n-nonyloxy group, and an n-decyloxy group.

Preferred examples of the —(—C($R^{16}$)$R^{17}$—)$n_1$-group include a —CH$_2$— group, a —CH(CH$_3$)— group, and a —CO— group, but the —(—C($R^{16}$)$R^{17}$—)$n_1$-group is not intended to be limited to these.

Z in the formulas (1), (2), and (3) represents an oxygen atom (—O—) or a sulfur atom (—S—).

k and j in the formula (1) each represent an integer of 0 or 1, and the sum j+k is not equal to 1. That is, when k is 1, j is also 1, and when k is 0, j is also 0. When k is 1, Y represents a hydrogen atom.

When j in the formula (1) is 1, X may be a hydrogen atom or a halogen atom, but X is preferably a halogen atom. Specifically, a preferred example of X is a chlorine atom.

The hydrogen atom of Y in the formulas (1), (2) and (3) and of X in the formula (1) may be an ordinary hydrogen atom, and may also be an isotope of a hydrogen atom. A preferred example of the isotope is a deuterium atom.

$Q^{\ominus}$ in the formula (2) represents a counter anion. Specific examples of the counter anion include alkyl- or arenesulfonyloxy ions such as a trifluoromethanesulfonyloxy ion (TfO$^-$), a p-toluenesulfonyloxy ion (TsO$^-$), a methanesulfonyloxy ion (MsO$^-$), and a benzenesulfonyloxy ion (BsO$^-$); and ions such as BF$_4^-$, SbF$_6^-$, CF$_3$COO$^-$, CH$_3$COO$^-$, PF$_6^-$, NO$_3^-$, ClO$_4^-$, SCN$^-$, OCN$^-$, ReO$_4^-$, MoO$_4^-$, BPh$_4^-$, B(C$_6$F$_5$)$_4^-$, and B(3,5-(CF$_3$)$_2$C$_6$F$_3$)$_4^-$.

The halogen atom represented by V in the formula (3) represents a chlorine atom, a bromine atom or an iodine atom, and all V's may represent an identical halogen atom, or may represent a combination of different halogen atoms.

The complex of the present invention can be synthesized by, for example, the method of the following Scheme (1).

Scheme 1

[Chem. 4]

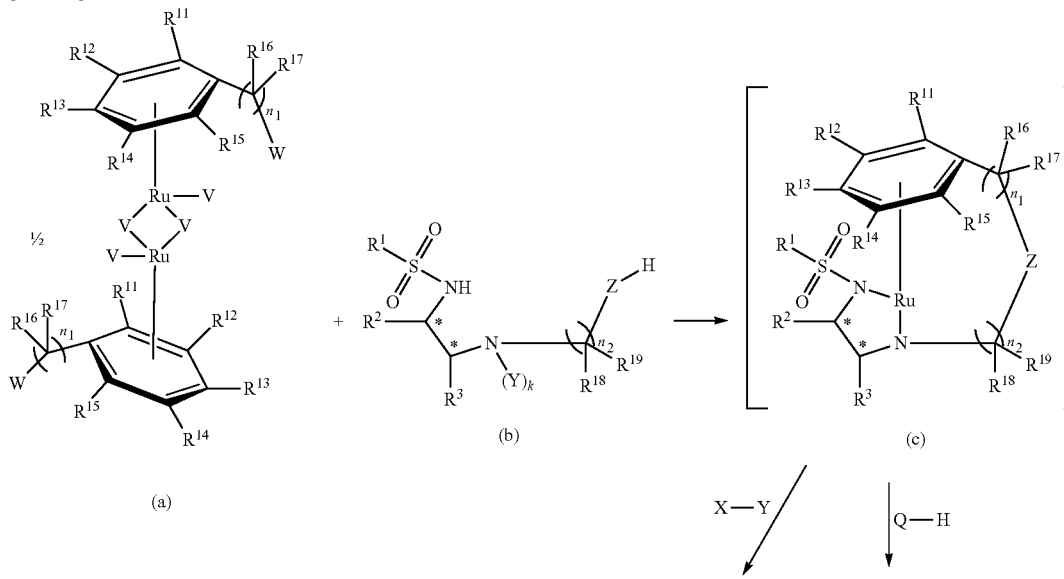

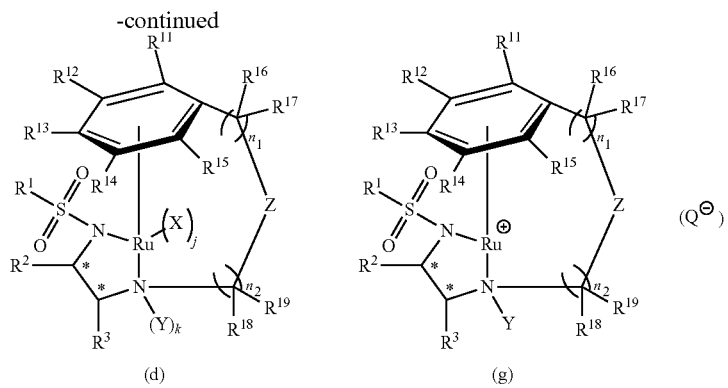

(d)    (g)

In the Scheme (1), $R^1$, $R^2$, $R^3$, $R^{11}$ to $R^{15}$, and $R^{16}$ to $R^{19}$ respectively represent the same substituents as defined above; Y represents a hydrogen atom or a deuterium atom; and Z represents an oxygen atom or a sulfur atom. W in the ruthenium-arene dimer (a) represents a halogen atom, or an alkanesulfonyloxy or optionally substituted arenesulfonyloxy group; and V represents a halogen atom. $n_1$ represents an integer of 1 or 2, and $n_2$ represents an integer from 1 to 3.

As shown in the Scheme (1), when a ruthenium-arene dimer (a) having a halogen atom or the like at a terminal of the substituent of the arene, is reacted with a diamine (b) having a hydroxyl group or a thiol group at a terminal of the chain-like portion substituted with a nitrogen atom that is other than the nitrogen atom substituted with a sulfonyl group, in the presence of an appropriate base, and thereby a thioetherification or etherification reaction is carried out simultaneously with complexation, a ruthenium-diamine complex (d), which is the target complex, can be synthesized directly or via an amido complex (c) as an intermediate. When the amide complex (c) is employed as an intermediate, the amido complex can be converted to a diamine complex (d) or a cationic diamine complex (g) by adding an appropriate acid to the complex (c).

Examples of the halogen atom or the alkanesulfonyloxy or optionally substituted arenesulfonyloxy group, which is represented by W in the ruthenium-arene dimer (a), include a chlorine atom, a bromine atom, an iodine atom, a methanesulfonyloxy group, a p-toluenesulfonyloxy group, a benzenesulfonyloxy group, and a trifluoromethanesulfonyloxy group. Furthermore, the halogen atom represented by V may be a chlorine atom, a bromine atom or an iodine atom, and all V's may represent an identical halogen atom, or may represent a combination of different halogen atoms.

Z in the diamine (b) represents an oxygen atom or a sulfur atom. Furthermore, Y represents a hydrogen atom.

Examples of the base that is used in case of synthesizing the amido complex (c) include inorganic bases such as LiOH, NaOH, KOH, $K_2CO_3$, and $Cs_2CO_3$; and metal alkoxides such as sodium methoxide and potassium methoxide. The amount of addition of the base is 2 moles or more relative to the amount of ruthenium atoms. There are no particular limitations on the solvent used in this case, but ethers such as diethyl ether and tetrahydrofuran; aromatic hydrocarbons such as toluene and xylene; halogen-containing hydrocarbon solvents such as dichloromethane and 1,2-dichloroethane; aprotic polar solvents such as acetonitrile and N,N-dimethylformamido; and the like are preferred, while dichloromethane and toluene are particularly preferred. Furthermore, this reaction can be carried out as a two-layer system reaction by using water as another solvent in addition to an organic solvent. In this case, the reaction may be carried out using a phase transfer catalyst. Examples of the phase transfer catalyst used in this case include tetrabutylammonium chloride, tetrabutylammonium bromide, tetrabutylammonium iodide, tetraethylammonium chloride, tetraethylammonium bromide, tetraethylammonium iodide, triethylbenzylammonium chloride, triethylbenzylammonium bromide, and triethylbenzylammonium iodide.

Examples of the acid (X—Y) used when the amido complex (c) is converted to a diamine complex (d) include hydrochloric acid, hydrobromic acid, and hydriodic acid.

Similarly, the amido complex (c) can also be converted to a cationic diamine complex (g). Examples of the acid (Q-H) used in this case include trifluoromethanesulfonic acid (TfOH), methanesulfonic acid (MsOH), p-toluenesulfonic acid (TsOH), benzenesulfonic acid (BsOH), $HBF_4$, $HSbF_6$, $CF_3COOH$, $CH_3COOH$, $HPF_6$, $HNO_3$, $HClO_4$, HSCN, HOCN, $HReO_4$, and $HMoO_4$.

There are no particular limitations on the solvent used to carry out this reaction; however, after the synthesis of the amido complex (c) described above, the amido complex (c) may be directly subjected to a reaction, without isolating the complex, in the presence of the same solvent within the system to be converted to the diamine complex (d) or (g), or alternatively, the amido complex (c) may be isolated and then subjected to a reaction using an appropriate, different solvent to be converted to the diamine complex (d) or the cationic diamine complex (g).

As the base used in the case of directly synthesizing the diamine complex (d), organic tertiary amines such as trimethylamine, triethylamine, triisopropylamine, and diisopropylethylamine are preferred, and particularly, triethylamine and diisopropylethylamine are suitable. The amount of addition of the base in this case is equimolar or greater relative to the amount of the ruthenium atoms.

There are no particular limitations on the solvent used in this case, but ethers such as diethyl ether and tetrahydrofuran; alcohols such as methanol, ethanol and isopropanol; aromatic hydrocarbons such as toluene and xylene; halogenic solvents such as dichloromethane and 1,2-dichloroehtane; aprotic polar solvents such as acetonitrile and N,N-dimethylformamide; and the like are preferred, while dichloromethane and isopropanol are particularly preferred.

Furthermore, as a method for synthesizing the complex of the present invention, a ruthenium-arene dimer (e) having a hydroxyl group or a thiol group at a terminal of the substituent of the arene, and a diamine (f) having a halogen atom or the like at a terminal of the chain-like portion substituted at a nitrogen atom that is other than the nitrogen atom substituted with a sulfonyl group, can also be used as raw materials, as shown in the following Scheme (2).

Scheme 2

[Chem. 5]

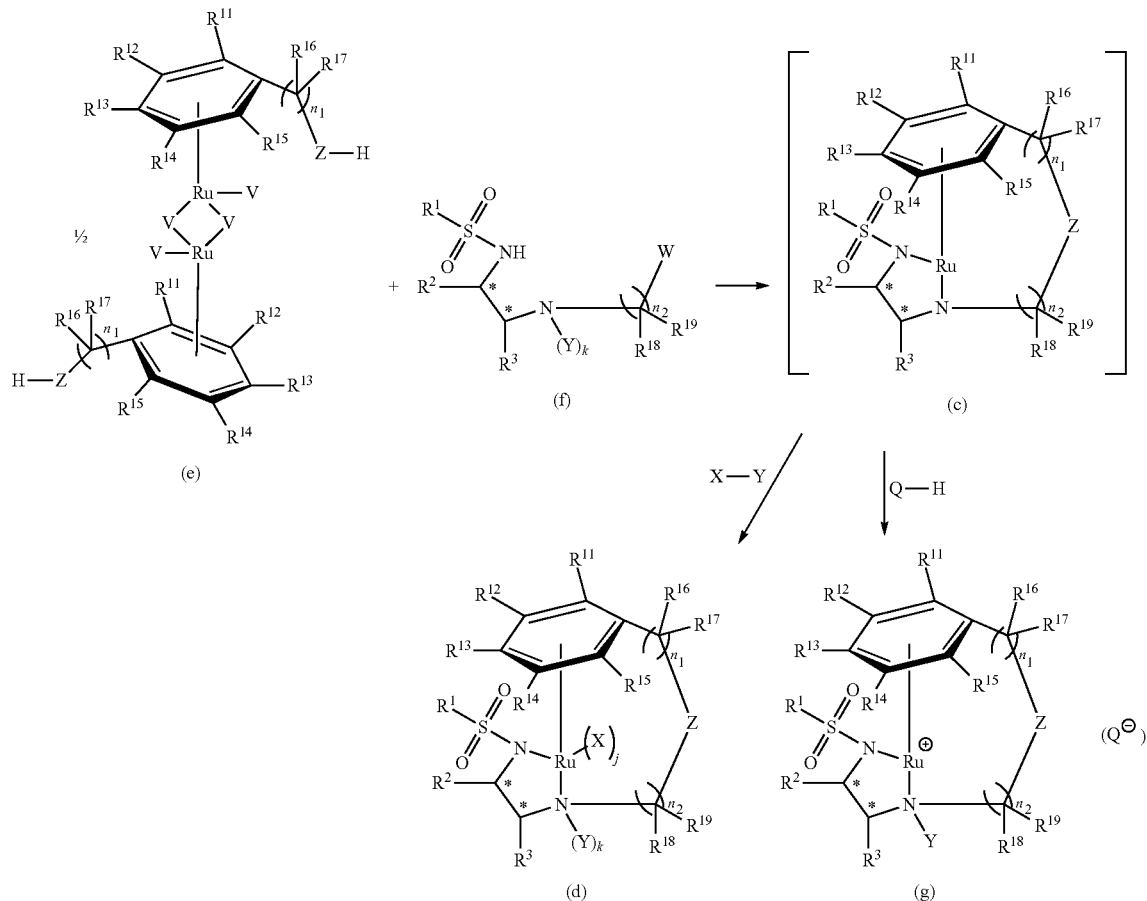

(The respective symbols in Scheme (2) have the same meanings as defined in Scheme (1)).

In the Scheme (2), the positions of the hydroxyl group or thiol group and the leaving group such as a halogen atom are the reverse of the combination used in the Scheme (1). However, the ruthenium-diamine complex (d) or the cationic diamine complex (g), which are both target complexes, can be similarly synthesized directly or via the amido complex (c), by allowing the hydroxyl group or thiol group and the leaving group to react in the presence of an appropriate base, and performing a thioetherification or etherification reaction simultaneously with complexation. When the amido complex (c) is employed as an intermediate, the amido complex can be converted to a diamine complex (d) or a cationic diamine complex (g) by adding an appropriate acid to the complex (c). The base, solvent and the like used in the reaction respectively have the same meanings as defined above.

Furthermore, the complex of the present invention can also be produced by a method such as shown in the following Scheme (3).

Scheme 3

[Chem. 6]

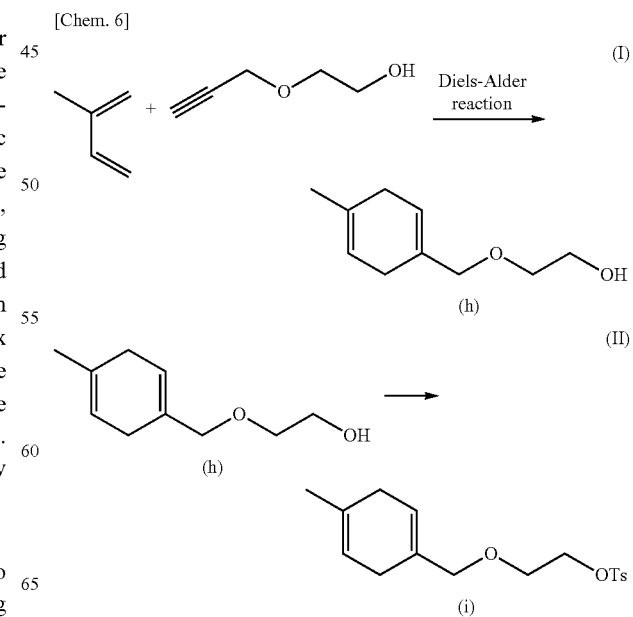

-continued

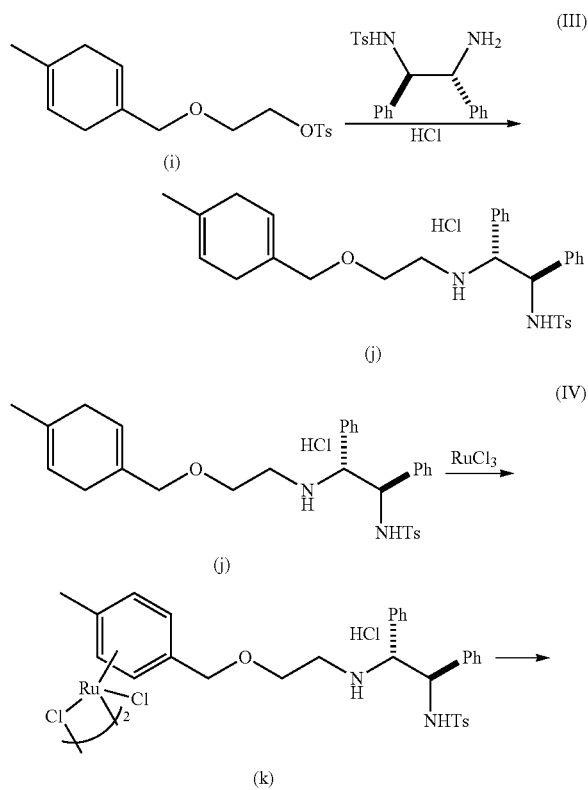

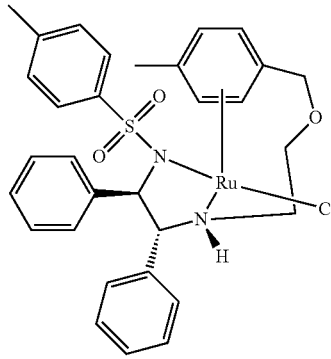

(I) A compound (h) having a 1,4-cyclohexadiene skeleton is synthesized by using the Diels-Alder reaction.

(II) The compound (h) obtained in the item (1) is subjected to tosylation or the like, and thereby a compound (i) having a leaving group at a terminal is synthesized.

(III) The compound (i) is made to react with TsDPEN (N-(p-toluensulfonyl)-1,2-diphenylethylenediamine), and thereby a diamine (j) having cyclohexadiene is synthesized.

(IV) The diamine (j) thus obtained is made to react with ruthenium trichloride to obtain a ruthenium dimer (k) as an intermediate, and thereby the target monomer complex is obtained.

Through this method, the ruthenium complex represented by the formula (1) and (3) of the present invention can be produced.

Furthermore, the ruthenium complexes represented by the formula (2) of the present invention can also be produced by a method such as shown in the following Scheme (4).

Scheme 4

[Chem. 7]

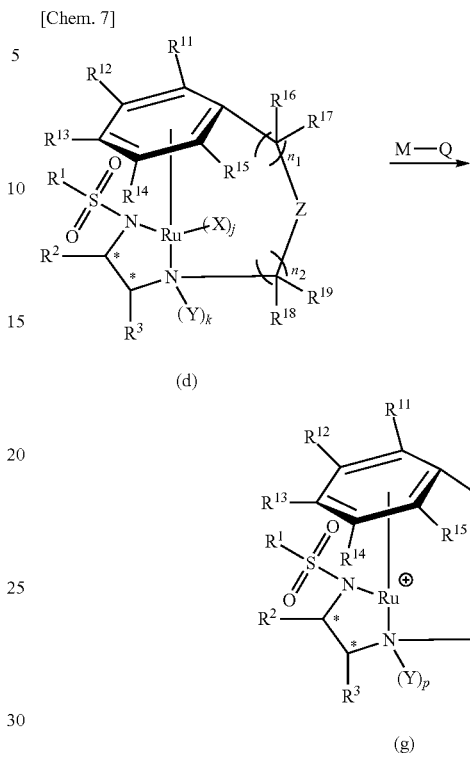

As shown in the Scheme (4), the cationic diamine complex (g) can also be obtained by allowing a diamine complex (d) in which X is a halogen atom, to react with a metal salt represented by the formula M-Q. Examples of the metal M in the formula: M-Q include silver (Ag), sodium (Na), potassium (K), and lithium (Li). Examples of the moiety Q include alkanesulfonyloxy or arenesulfonyloxy compounds such as trifluoromethanesulfonyloxy (TfO), p-toluenesulfonyloxy (TsO), methanesulfonyloxy (MsO), and benzenesulfonyloxy (BsO); as well as $BF_4$, $SbF_6$, $CF_3COO$, $CH_3COO$, $PF_6$, $NO_3$, $ClO_4$, SCN, OCN, $ReO_4$, $MoO_4$, $BPh_4$, $B(C_6F_5)_4$, and $B(3,5-(CF_3)_2C_6F_3)_4$.

Examples of the metal salt represented by the formula: M-Q include AgOTf, AgOTs, AgOMs, AgOBs, $AgBF_4$, $AgSbF_6$, $CF_3COOAg$, $CH_3COOAg$, $AgPF_6$, $AgNO_3$, $AgClO_4$, AgSCN, AgOCN, $AgReO_4$, $AgMoO_4$, NaOTf, $NaBF_4$, $NaSbF_6$, $CF_3COONa$, $CH_3COONa$, $NaPF_6$, $NaNO_3$, $NaClO_4$, NaSCN, KOTf, $KBF_4$, $KSbF_6$, $CF_3COOK$, $CH_3COOK$, $KPF_6$, $KNO_3$, $KClO_4$, KSCN, $KBPh_4$, $KB(C_6F_5)_4$, $KB(3,5-(CF_3)_2C_6F_3)_4$, LiOTf, $LiBF_4$, $LiSbF_6$, $CF_3COOLi$, $CH_3COOLi$, $LiPF_6$, $LNO_3$, $LiClO_4$, LiSCN, $LiBPh_4$, $LiB(C_6F_5)_4$, and $LiB(3,5-(CF_3)_2C_6F_3)_4$.

The amount of the metal salt M-Q that is used in the case of synthesizing the cationic diamine complex (g) is equimolar or greater relative to the amount of ruthenium atoms. There are no particular limitations on the solvent used in this case, but examples of the solvent include alcohols such as methanol, ethanol, and isopropanol; aromatic hydrocarbons such as toluene and xylene; halogenated hydrocarbons such as dichloromethane and 1,2-dichloroethane; aprotic polar solvents such as acetonitrile and N,N-dimethylformamido; and ethers such as diethyl ether and tetrahydrofuran. Among these, methanol is preferred.

As such, the ruthenium complex of the present invention having a heteroatom introduced into the chain-like moiety can be synthesized using an appropriate ruthenium-arene dimer and an appropriate diamine, by carrying out a thioetherification or etherification reaction simultaneously with the formation of the complex, and thereby a complex having a side chain that links the arene portion and the diamine portion can be synthesized. Theoretically, in this reaction, the complex can be produced by allowing the ruthenium-arene dimer to react in an equimolar amount, in terms of ruthenium, based on the diamine, and therefore, the reaction is very efficient. Also, since the reactions used in this synthesis method are all reaction that are carried out under the conditions ranging from normal temperature to a heating condition, it is not necessary to use cryogenic apparatuses, and harmful gases and the like are not generated. Thus, this method is a synthesis method which is very simple, safe and expedient when synthesis is carried out in an industrial scale.

The ruthenium complex of the present invention in which X is a halogen atom can be readily converted to a complex in which X is a hydrogen atom by bringing the ruthenium complex into contact with a hydrogen donor.

Here, as the hydrogen donor, those generally used as hydrogen donors in hydrogen transfer type reduction reactions of a metal hydride such as a borohydride compound, formic acid or a salt thereof, isopropanol and the like, can be used. The amount of use of the hydrogen donor may be an equimolar amount or greater, in terms of hydride, relative to the amount of the catalyst. Furthermore, hydrogen gas can also be used as a hydrogen donor.

Furthermore, examples of the base that is used to obtain basic conditions include organic tertiary amines such as trimethylamine, triethylamine, and triisopropylamine; inorganic bases such as LiOH, NaOH, KOH, and $K_2CO_3$; and metal alkoxides such as sodium methoxide, and potassium methoxide.

Furthermore, conversion of a halogen atom to a hydrogen atom for X in the ruthenium complex of the present invention may be carried out in advance before the reaction system is subjected to the asymmetric reduction reaction, or may also be carried out in the middle of the asymmetric reduction reaction.

The production of the ruthenium complex of the present invention is usually carried out at 120° C. or below, and preferably at 100° C. or below.

The asymmetric reduction reaction may be carried out by using a compound obtained by isolating the amido complex (c), the diamine complex (d), the cationic diamine complex (g), or the ruthenium dimer(k) as a catalyst, or may also be carried out without isolating the complex, by directly using the reaction liquid resulting from the production of a complex (in situ method).

After completion of the reaction, the intended ruthenium complex can be separated by a general precipitation technique such as concentration of the reaction liquid or addition of a poor solvent. Furthermore, if a hydrogen halide salt is produced as a side product during the production described above, an operation of water washing may be performed as necessary.

The asymmetric reduction reaction of the present invention is carried out by allowing a ruthenium complex represented by the formula (1) to react with a carbonyl compound or an imine in the co-presence of a hydrogen donor. There are no particular limitations on the hydrogen donor, as long as it is a hydrogen donor that is generally used in hydrogen transfer reduction reactions of formic acid or a salt thereof, isopropanol which is an alcohol having a hydrogen atom on the α-position carbon atom substituted with a hydroxyl group, and the like. Furthermore, hydrogen gas can also be used as the hydrogen donor. Also, it is preferable that the asymmetric reduction reaction be carried out in the presence of a base. Examples of the base include organic tertiary amines such as trimethylamine, triethylamine, triisopropylamine, 1,4-diazabicyclo[2,2,2]octane (DABCO), and 1,8-diazabicyclo[5,4,0]undec-7-ene (DBU); and inorganic bases such as LiOH, NaOH, KOH, and $K_2CO_3$. A suitable base is triethylamine. The base is used in an excess amount, for example, in an amount of 1 to 100,000 times on a molar basis, relative to the amount of the ruthenium complex. In the case of using triethylamine, it is preferable to use the base in an amount of 1 to 10,000 times relative to the amount of the catalyst.

In the combination of a hydrogen donor and a base, when the hydrogen donor is formic acid, it is preferable to use an amine as the base. In this case, formic acid and the amine may be added separately to the reaction system, but an azeotropic mixture of formic acid and an amine may be prepared in advance and used. A preferred example of the azeotropic mixture of formic acid and an amine may be a formic acid-triethylamine (5:2) azeotropic mixture, or the like.

The reaction is usually carried out such that when the hydrogen donor is a liquid, the hydrogen donor can be utilized as a reaction solvent. However, in order to dissolve the raw materials, a non-hydrogen-donating solvent such as toluene, tetrahydrofuran, acetonitrile, dimethylformamide, dimethyl sulfoxide, acetone, or methylene chloride can also be used singly or in mixture as an auxiliary solvent. In the case of using a formic acid salt or the like, water is used as an auxiliary solvent, together with an organic solvent, in order to dissolve the formic acid salt, and the reaction may be carried out in a two-layer system. In this case, a phase transfer catalyst may be used together in order to accelerate the reaction. Furthermore, in the case of using hydrogen gas, an alcohol solvent such as methanol, ethanol, isopropanol, trifluoroethanol, or hexafluoro-2-propanol is preferred.

The amount of use of the ruthenium complex as a catalyst is selected such that the molar ratio (S/C) of the substrate (a carbonyl compound or an imine) (S) with respect to ruthenium metal atoms (C) is in the range of 10 to 1,000,000, and preferably 100 to 15,000.

In regard to the amount of the hydrogen donor relative to the amount of the carbonyl compound or the imine, usually an equimolar amount or greater is used, and inter alia, when the hydrogen donor is formic acid or a salt thereof, the amount of the hydrogen donor is preferably a 1.5-fold molar amount or greater. Furthermore, the hydrogen donor is used in an amount in the range of a 20-fold molar amount or less, and preferably a 10-fold molar amount or less. On the other hand, when the hydrogen donor is isopropanol or the like, the hydrogen donor is used in a large excess based on the substrate from the viewpoint of reaction equilibrium, and the hydrogen donor is usually used in an amount in the range of a 1000-fold molar amount or less.

The reaction temperature is selected in the range of −20° C. to 100° C., and preferably 0° C. to 70° C.

The reaction pressure is not particularly limited, and the reaction is usually carried out at 0.05 to 0.2 MPa, and preferably at normal pressure.

Furthermore, in the case of using hydrogen gas, the pressure is usually 5 MPa or less.

The reaction time may vary depending on the catalyst ratio, but the reaction time is 1 to 100 hours, and usually 2 to 50 hours.

After the reaction, the optically active substance thus produced can be separated and purified by general operations such as distillation, extraction, chromatography, and recrystallization.

EXAMPLES

Hereinafter, the present invention will be described in detail by way of Examples, but the present invention is not intended to be limited thereto.

The NMR spectra used in the identification of complexes and the determination of purity in the following Examples were measured using a Mercury Plus 300 4N type apparatus manufactured by Varian Technologies Japan, Ltd., or a Bruker BioSpin Avance III 500 System. Furthermore, the GC analysis was carried out using Chirasil-DEX CB (0.25 mm×25 m, 0.25 μm) (manufactured by Varian, Inc.), Inert-CapPure-WAX(0.25 mm×30 m, 0.25 μm) (GL Sciences Inc.) and the HPLC analysis was carried out using CHIRALCEL OJ-H (0.46 mm×25 cm) (manufactured by Daicel Chemical Industries, Ltd.).

The symbols in the Examples have the following meanings.

MsDPEN: N-methanesulfonyl-1,2-diphenylethylenediamine

TsDPEN: N-(p-toluensulfonyl)-1,2-diphenylethylenediamine o-TFTsDPEN: N-(2-trifluorotoluenesulfonyl)-1,2-diphenylethylenediamine TIPPsDPEN: N-(2,4,6-triisopropylbenzenesulfonyl)-1,2-diphenylethylenediamine MESsDPEN: N-(2,4,6-trimethylbenzenesulfonyl)-1,2-diphenylethylenediamine TsCYDN: N-(p-toluenesulfonyl)-1,2-cyclohexanediamine MIBK: Methyl isobutyl ketone dppe: Diphenylphosphinoethane DIPEA: Diisopropylethylamine However, the diamine in the complex represents that one or two hydrogen atoms of the diamine have been detached.

The term S/C represents the value of the ratio (mole number of substrate/mole number of catalyst).

Example 1

Production of N-((1R,2R)-1,2-diphenyl-2-(2-(tetrahydro-2H-pyran-2-yloxy)ethylamino)ethyl)-4-methylbenzenesulfonamide The target compound (B) was produced by the reaction shown below.

[Chem. 8]

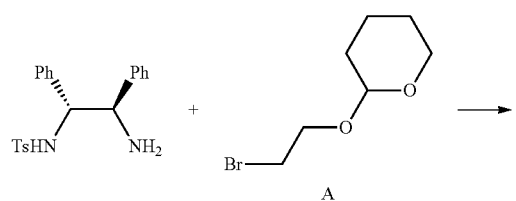

-continued

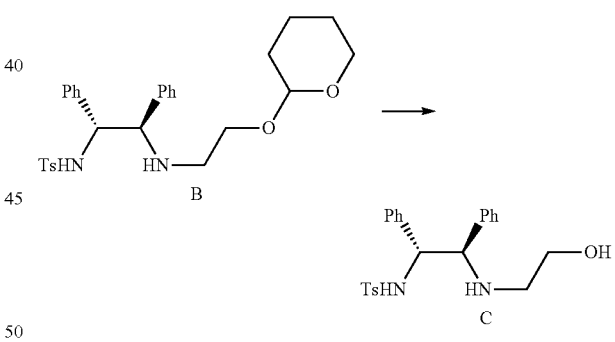

In a 50-ml Schlenk tube, 5.0 g (13.65 mmol) of (R,R)-TsDPEN and 2.85 g (2.07 ml) (13.65 mmol) of an alkyl bromide (A) were mixed with 10 ml of DMSO, and the mixture was allowed to react for 29 hours at 60° C. Subsequently, 50 ml of dichloromethane and 50 ml of a saturated aqueous solution of NaHCO$_3$ were introduced into the reaction mixture, and the resulting mixture was stirred. Subsequently, the organic layer was separated and was washed two more times with 50 ml of a saturated aqueous NaHCO$_3$. Dichloromethane was recovered, and the residue was purified by silica gel column chromatography. Thus, 4.94 g (72% yield) of the desired compound (B) was obtained.

$^1$H-NMR(CDCl$_3$, 300 MHz) δ:
1.43-1.80 (m, 6H), 2.32 (s, 3H), 2.42-2.70 (m, 21-1), 3.40-3.55 (m, 2H), 3.70-3.85 (m, 2H), 3.77 (d, 1H), 4.30 (m, 1H), 4.45 (d, 1H), 6.93-7.38 (m, 14H)

Example 2

Production of N-((1R,2R)-2-(2-hydroxyethylamino)-1,2-diphenylethyl)-4-methylbenzenesulfonamide The target diamine (C) was produced by the reaction shown below.

[Chem. 9]

135 ml of ethanol and 34.5 ml of a 1 M aqueous solution of HCl were added to 5.69 g of the compound (B) obtained in Example 1 as described above, and the mixture was allowed to react for 2 hours at 40° C. Subsequently, 3.45 g of NaHCO$_3$ was added to the reaction mixture to neutralize the solution, and then 75 ml of water and 150 ml of diethyl ether were added thereto. The reaction mixture was separated. Subsequently, 50 ml of water was added, and the ether was removed with an evaporator. Thus, white crystals were precipitated. The reaction mixture was ice-cooled and filtered. The filter cake was washed with water, and then was dried at 70° C. under reduced pressure. Thus, 4.33 g (92% yield) of the desired diamine (C) was obtained.

$^1$H-NMR(CDCl$_3$, 300 MHz) δ:
2.31 (s, 3H), 2.50-2.62 (m, 2H), 3.58-3.75 (m, 2H), 3.79 (d, 1H), 4.40 (d, 1H), 6.82-7.41 (m, 14H)

Example 3

Production of N-((1S,2S)-1,2-diphenyl-2-(2-(tetrahydro-2H-pyran-2-yloxy)ethylamino)ethyl)methanesulfonamide The target compound (D) was produced by the reaction shown below.

[Chem. 10]

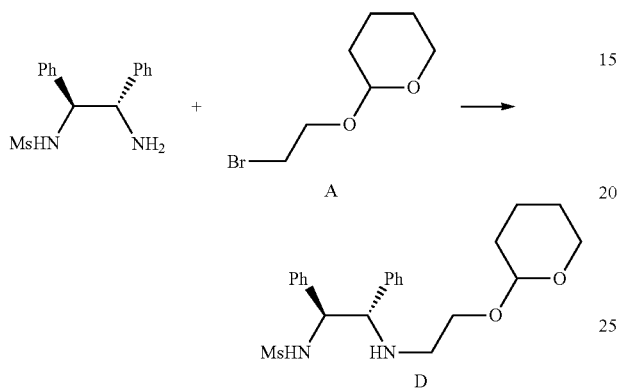

In a 50-ml Schlenk tube, 7.0 g (24.1 mmol) of (S,S)-MsDPEN and 5.04 g (3.64 ml, 24.1 mmol) of an alkyl bromide (A) were mixed with 17.6 ml of DMSO, and the mixture was allowed to react for 30 hours at 60° C. Subsequently, 50 ml of dichloromethane and 50 ml of a saturated aqueous solution of $NaHCO_3$ were introduced into the reaction mixture, and the resulting mixture was stirred. Subsequently, the organic layer was separated and was washed two more times with 50 ml of a saturated aqueous $NaHCO_3$. Dichloromethane was recovered, and the residue was purified by silica gel column chromatography. Thus, 5.06 g (50% yield) of the desired compound (D) was obtained.

$^1$H-NMR(CDCl$_3$, 300 MHz) δ:

1.42-1.90 (m, 6H), 2.20 (d, 3H), 2.50-2.75 (m, 2H), 3.40-3.50 (m, 2H), 3.70-3.83 (m, 2H), 3.90 (d, 1H), 4.45 (m, 1H), 4.50 (d, 1H), 7.10-7.30 (m, 10H)

Example 4

Production of N-((1S,2S)-2-(2-hydroxyethylamino)-1,2-diphenylethyl)methanesulfonamide The target diamine (E) was produced by the reaction shown below.

[Chem. 11]

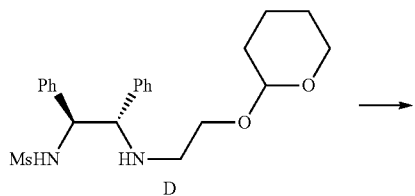

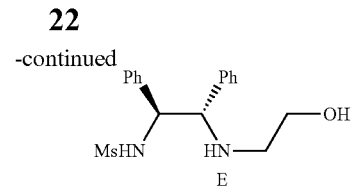

142 ml of ethanol and 38.7 ml of a 1 M aqueous solution of HCl were added to 5.06 g of the compound (D) obtained in Example 3 as described above, and the mixture was allowed to react for 2 hours at 40° C. Subsequently, 3.63 g of $NaHCO_3$ was added to the reaction mixture to neutralize the solution, and then 147 ml of water and 200 ml of diethyl ether were added thereto. The ether layer was separated. The aqueous layer was extracted two times with ether, and the ether layers thus obtained were combined, dried over $Na_2SO_4$, and then concentrated in an evaporator. Thus, 3.62 g (90% yield) of the desired diamine (E) was obtained.

$^1$H-NMR(CDCl$_3$, 300 MHz) δ:

2.40 (s, 3H), 2.50-2.72 (m, 2H), 3.60-3.75 (m, 2H), 3.93 (d, 1H), 4.57 (d, 1H), 7.10-7.24 (m, 10H)

Example 5

Production of (4-methylcyclohexa-1,4-dienyl)methanol

The target compound (F) was produced by the reaction shown below.

[Chem. 12]

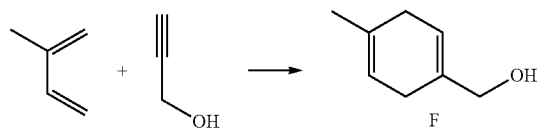

In a 500-ml four-necked flask, 1.73 g (7.93 mmol) of $CoBr_2$, 8.4 g (26.3 mmol) of $ZnI_2$, 3.47 g (8.8 mmol) of dppe, and 370 ml of dichloromethane were introduced, the flask was then purged with nitrogen, and the mixture was stirred for 30 minutes at 30° C. Subsequently, 78 ml (53.1 g, 780 mmol) of isoprene, 41 ml (39.3 g, 701 mmol) of propargyl alcohol, and 2.2 g (8.53 mmol) of $Bu_4NBH_4$ were fed to the flask, and the resulting mixture was allowed to react for 7 hours at 30° C. Subsequently, the dichloromethane solution was recovered and was distilled under reduced pressure at 160° C. Thus, 27.7 g (32% yield) of the desired diene mixture (F) was obtained. The purity of the target diene in this mixture as determined by gas chromatography (GC) was approximately 98%.

$^1$H-NMR(CDCl$_3$, 300 MHz) δ:

1.67 (s, z, 3H), 2.55-2.70 (m, 4H), 4.02 (s, 2H), 5.44 (m, 1H), 5.68 (m, 1H)

Example 6

Production of [RuCl$_2$(1-(bromomethyl)-4-methylbenzene)]$_2$

The target complex compound (G) was produced by the reaction shown below.

[Chem. 13]

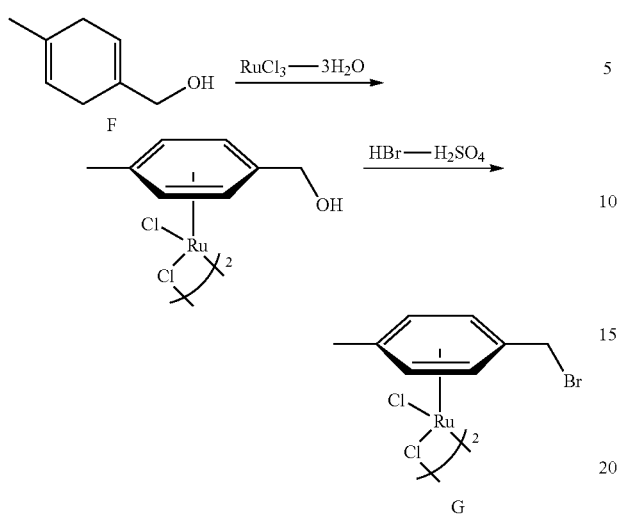

4.75 g (38.2 mmol) of the diene (F) obtained in Example 5 as described above, 2.0 g (7.65 mmol) of ruthenium trichloride trihydrate, and 0.643 g (7.65 mmol) of NaHCO$_3$ were dissolved in 40 ml of 2-methoxyethanol and 4 ml of water, and the solution was allowed to react for 1.5 hours at 130° C. Subsequently, the solvent was distilled off in an evaporator, and 52 ml of a concentrated aqueous solution of hydrobromic acid and 4 ml of concentrated sulfuric acid were added to the residue. The resulting mixture was stirred for 4 hours at 100° C. The solution obtained after the reaction was mixed with dichloromethane, water, and 2-methoxyethanol, and the mixture was stirred and left to stand still. Crystals precipitated therefrom were filtered, and thus 1.9 g (79% yield) of the desired complex (G) was obtained.

$^1$H-NMR(DMSO-d$_6$, 300 MHz) δ:

2.23 (s, 3H), 4.40 (s, 2H), 5.84 (d, 2H), 6.15 (d, 2H)

Example 7

Production of RuCl(R,R)—O-HT-Tsdpen)

The target complex, RuCl((R,R)—O-HT-Tsdpen), was produced by the reaction shown below.

[Chem. 14]

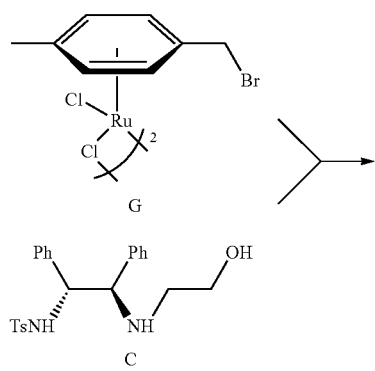

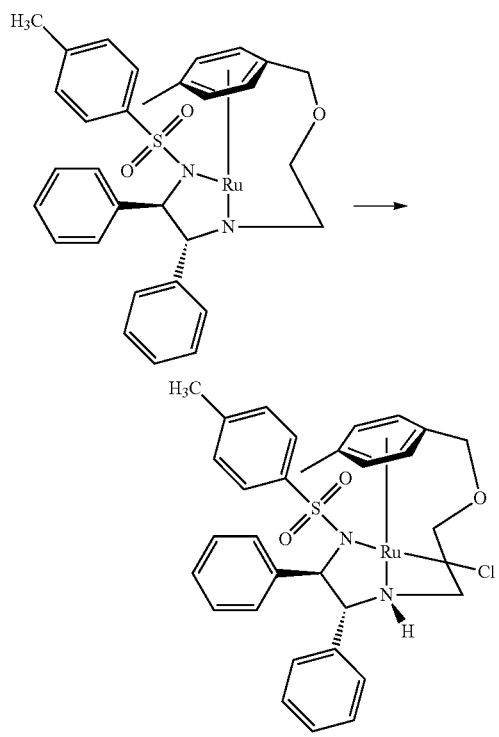

1.6 g (2.24 mmol) of the arene dimer (G) obtained in Example 6 as described above, 1.53 g (3.73 mmol) of the diamine (C) produced in Example 2, 1.19 g (3.73 mmol) of triethylbenzylammonium iodide (Et$_3$BnNI), 52.8 ml of dichloromethane, and 52.8 ml of water were mixed, and the mixture was stirred at 35° C. 1.78 g (26.9 mmol) of KOH was added to the mixture, and the resulting mixture was allowed to react for 3 hours. The organic layer turned into a purple solution. The reaction mixture was left to stand, and then the aqueous layer was removed. 50 ml of water was added to the organic layer, the mixture was stirred and then left to stand, and the aqueous layer was removed. This operation was repeated three times, and then 65 ml of a 0.1 M aqueous solution of HCl was added to the organic layer. The mixture was stirred for 30 minutes. Thereafter, 0.034 g of NaHCO$_3$ was added thereto to neutralize the solution, and then the mixture was left to stand. Only the dichloromethane layer was collected and dried to solid. This solid was purified with a silica gel column (eluent: CHCl$_3$/MeOH=20/1), and thus 1.1 g (45% yield) of the desired complex, RuCl(R,R)—O-HT-Tsdpen), was obtained (the purity determined by liquid chromatography (HPLC) was approximately 95%).

$^1$H-NMR(CD$_2$Cl$_2$, 300 MHz) δ:

2.25 (s, 3H), 2.52 (s, 3H), 3.13 (m, 1H), 3.60 (m, 1H), 3.80-4.00 (m, 4H), 4.48 (d, J=15.0 Hz, 1H), 4.52 (brs, 1H), 4.95 (d, J=15.0 Hz, 1H), 5.45 (d, J=5.2 Hz, 1H), 5.75 (d, J=6.2 Hz, 1H), 6.05 (d, J=5.2 Hz, 1H), 6.60 (d, J=6.9 Hz, 2H), 6.65-6.70 (m, 4H), 6.88 (d, J=8.0 Hz, 2H), 7.08-7.18 (m, 4H), 7.23 (d, J=8.0 Hz, 2H)

HRMS (ESI):

As C$_{31}$H$_{33}$N$_2$O$_3$RuS.

Calculated value: [M–Cl]$^+$ 615.1258.

Found value: 615.1258.

Example 8

Asymmetric Hydrogen Transfer Reaction of Acetophenone Using the Complex RuCl((R,R)—O-HT-Tsdpen) (S/C=2000)

In 50-ml Schlenk tube, 6.5 mg (0.01 mmol) of the complex RuCl(R,R)—O-HT-Tsdpen) produced in Example 7 as described above, 2.32 ml (2.40 g, 20 mmol) of acetophenone, and 10 ml of a formic acid-triethylamine (5:2) azeotropic mixture were mixed, and the Schlenk tube was purged with nitrogen. Subsequently, the mixture was allowed to react for 24 hours at 60° C. An analysis of the reaction liquid was carried out by GC, and it was found that (R)-1-phenylethanol with 96.3% ee was produced at a conversion rate of 97.5%.

Example 9

Production of RuCl((S,S)—O-HT-Msdpen)

The target complex, RuCl((S,S)—O-HT-Msdpen), was produced by the reaction shown below.

[Chem. 15]

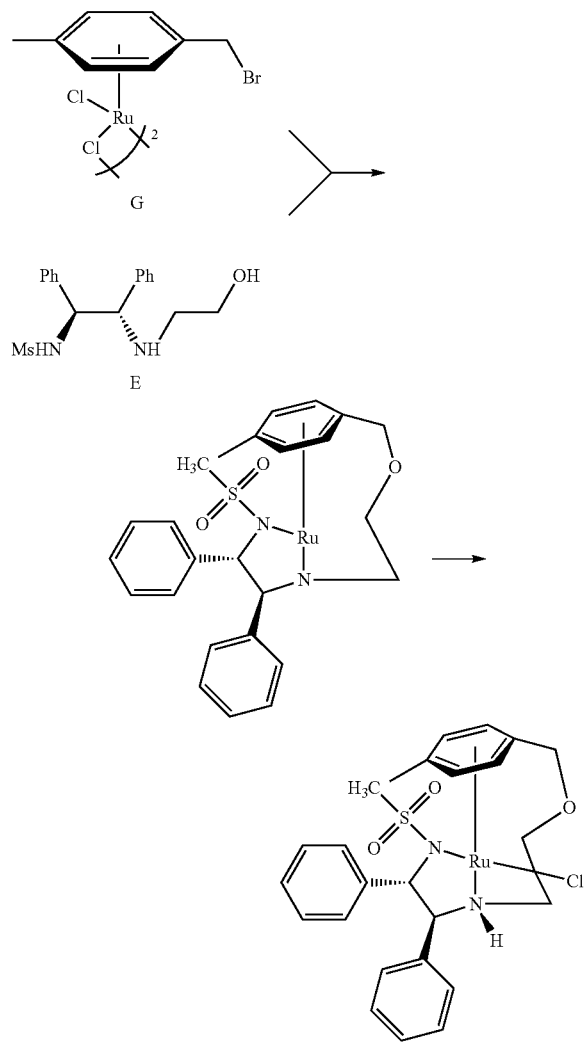

1.7 g (2.38 mmol) of the arene dimer (G) produced in Example 6, 1.325 g (3.96 mmol) of the diamine (E) produced in Example 4, 1.26 g (3.96 mmol) of triethylbenzylammonium iodide ($Et_3BnNI$), 56 ml of dichloromethane, and 56 ml of water were mixed. While the mixture was stirred at 35° C., 1.78 g (26.9 mmol) of KOH was added to the mixture, and the mixture was allowed to react for 3 hours. The organic layer turned into a purple solution. After the mixture was left to stand, the aqueous layer was removed, 50 ml of water was added thereto, and the mixture was stirred. Subsequently, the mixture was left to stand and the aqueous layer was removed. This operation was carried out three times, and then 68 ml of a 0.1 M aqueous solution of HCl was added to the organic layer. The resulting mixture was stirred for 30 minutes. Thereafter, 1.88 g of $NaHCO_3$ was added to neutralize the solution, and then the mixture was left to stand. Only the dichloromethane layer was collected and dried to solid. This solid was purified with a silica gel column (eluent: $CHCl_3$/MeOH=20/1), and thus 0.98 g (43% yield) of the desired complex, RuCl((S,S)—O-HT-Msdpen), was obtained (the purity determined by HPLC was approximately 95%).

$^1$H-NMR($CD_2Cl_2$, 300 MHz) δ:

2.42 ((s, 3H($CH_3$ of Ms)), (s, 3H($CH_3$ of tolyl))), 3.17-3.25 (m, 1H), 3.32-3.40 (m, 1H), 4.00 (d, 1H), 3.90-4.02 (m, 2H), 4.10 (d, 1H), 4.20-4.30 (br, 1H), 4.62-4.75 (br, 2H), 5.50 (d, J=6.0 Hz, 1H), 5.63 (br, 1H), 5.75 (br, 1H), 5.88 (d, J=6.0 Hz, 1H), 6.84-6.88 (m, 2H), 6.98-7.03 (m, 2H), 7.10-7.20 (m, 6H)

HRMS (ESI):

As $C_{26}H_{29}N_2O_3RuS$.

Calculated value: $[M-Cl]^+$ 539.0942.

Found value: 539.0946.

Example 10

Asymmetric Hydrogen Transfer Reaction of Acetophenone Using RuCl(S,S)—O-HT-Msdpen) (S/C=5000)

In 50-ml Schlenk tube, 2.2 mg (0.0039 mmol) of RuCl((S,S)—O-HT-Msdpen) produced in Example 9 as described above, 2.24 ml (2.31 g, 19.3 mmol) of acetophenone, and 9.7 ml of a formic acid-triethylamine (5:2) azeotropic mixture were mixed, and the Schlenk tube was purged with nitrogen. Subsequently, the mixture was allowed to react for 24 hours at 60° C. An analysis of the reaction liquid was carried out by GC, and it was found that (S)-1-phenylethanol with 94.7% ee was produced at a conversion rate of 95.6%.

Example 11

Production of Ru((R,R)—O-HT-Tsdpen) and Hydrogen Transfer Reaction (In Situ Method) of Acetophenone Using the Complex The complex Ru((R,R)—O-HT-Tsdpen) was produced by the reaction shown below, and a hydrogen transfer reaction of acetophenone was carried out in situ using the complex (in situ method).

[Chem. 16]

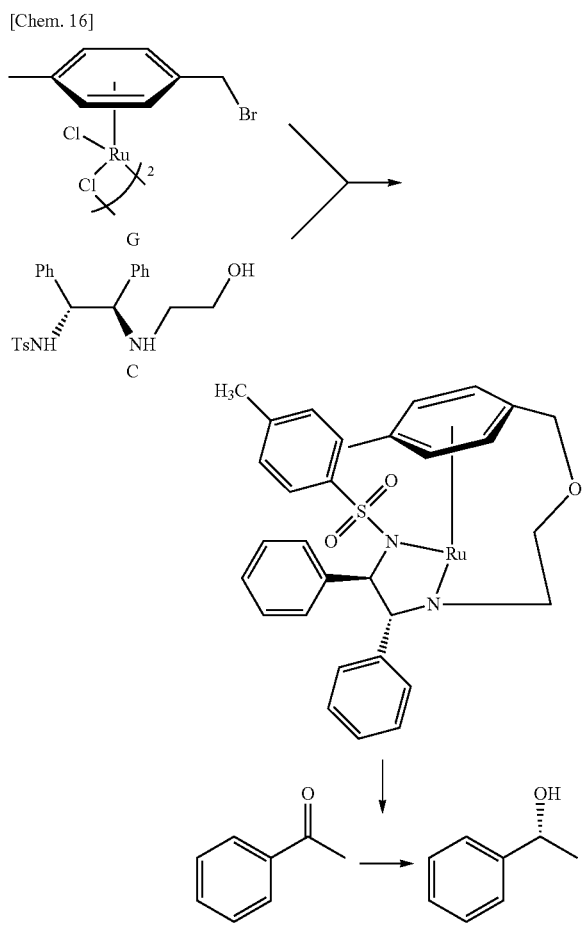

18.0 mg (0.025 mmol) of the arene dimer (G) produced in example 6, 17.2 mg (0.042 mmol) of the diamine (C) produced in Example 2, 13.4 mg (0.042 mmol) of triethylbenzylammonium iodide (Et$_3$BnNI), 0.6 ml of dichloromethane, and 0.6 ml of water were mixed, and while the mixture was stirred at 35° C., 0.02 g (0.3 mmol) of KOH was added to the mixture. The resulting mixture was allowed to react for 6 hours. The organic layer turned into a purple solution. The reaction liquid was left to stand, and 36 μl of the reaction liquid was evacuated from the organic layer to apply to the reduction for the catalyst ratio was S/C=2000. The catalyst solution was added to a 15-ml Schlenk tube, and 0.58 ml (0.6 g, 5.0 mmol) of acetophenone and 2.5 ml of a formic acid-triethylamine (5:2) azeotropic mixture were incorporated therein. The Schlenk tube was purged with nitrogen, and then the mixture was allowed to react for 24 hours at 60° C. An analysis of the reaction liquid was carried out by GC, and it was found that (R)-1-phenylethanol with 96.2% ee was produced at a conversion ratio of 96.5%.

Example 12

Production of N-((1R,2R)-2-(2-mercaptoethylamino)-1,2-diphenylethyl)-4-methylbenzenesulfonamide The target mercaptodiamine (H) was produced by the reaction shown below.

[Chem. 17]

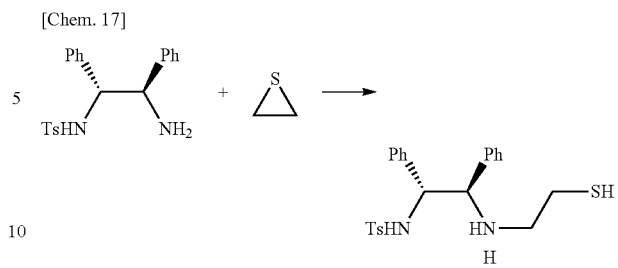

In a 50-ml glass autoclave, 5.0 g (13.6 mmol) of (R,R)-TsDPEN, 0.758 g (0.75 ml) (13.6 mmol) of ethylene sulfide, and 25 ml of toluene were mixed, and the mixture was allowed to react for 48 hours at 120° C. Subsequently, toluene was recovered, and the residue was purified by silica gel column chromatography. Thus, 3.2 g (55% yield) of the desired mercaptodiamine (H) was obtained.

$^1$H-NMR(CD$_2$Cl$_2$, 300 MHz) δ:

0.58 (br, 2H), 1.94 (s, 3H), 2.10-2.33 (m, 4H), 3.53 (d, 1H), 4.59 (d, 1H), 6.36 (br, 1H), 6.69 (d, 2H), 6.79 (m, 8H), 6.93-7.00 (m, 8H), 7.64 (d, 2H)

Example 13

Production of the Complex RuCl(R,R)—S-HT-Tsdpen)

The target complex RuCl((R,R)—S-HT-Tsdpen) was produced by the reaction shown below.

[Chem. 18]

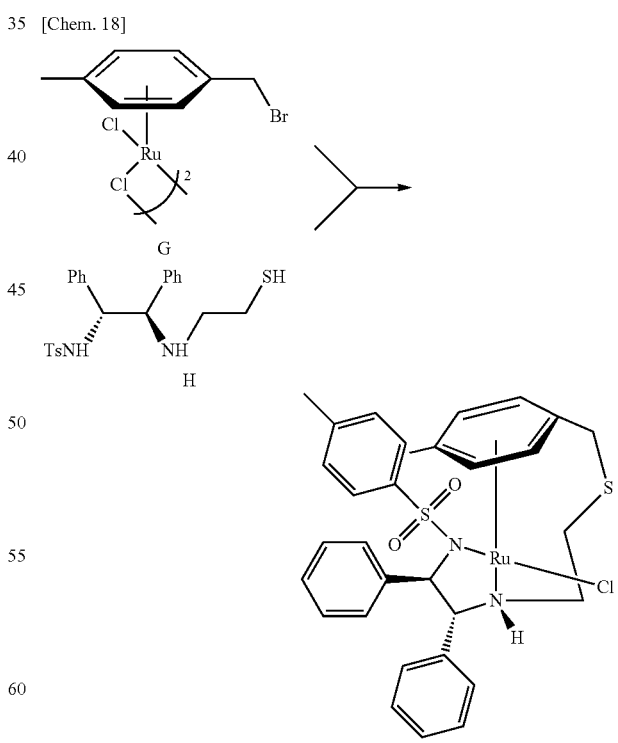

0.1 g (0.234 mmol) of the arene dimer (G) produced in Example 6, 0.1 g (0.14 mmol) of the mercaptodiamine (H) produced in Example 12, 0.121 g (163 μl, 0.936 mmol) of DIPEA (Hunig's Base), and 2 ml of dichloromethane were mixed, and the mixture was allowed to react at 45° C. Subsequently, three times operation of adding water, stirring the mixture, subsequently leaving the mixture to stand, washing the organic layer was carried out, and the organic layer was dried to solid. Thus, a solid mixture containing the desired complex, RuCl((R,R)—S-HT-Tsdpen), was obtained.

HRMS (ESI): As $C_{31}H_{33}N_2O_2RuS_2$.
Calculated value: $[M-Cl]^+$ 631.1028.
Found value: 631.1012.

Example 14

Asymmetric Hydrogen Transfer Reaction of Acetophenone Using a Complex RuCl((R,R)—S-HT-Tsdpen)

A hydrogen transfer reaction of acetophenone was carried out in a formic acid-triethylamine (5:2) azeotrope with S/C=600 at 60° C. After the reaction was carried out for 16 hours, an analysis of the reaction liquid was carried out by GC, and it was found that (R)-1-phenylethanol with 77.9% ee was produced at a conversion ratio of 67.0%.

Example 15

Asymmetric hydrogen transfer reaction of propiophneone using a complex RuCl((R,R)—O-HT-Tsdpen)

In a 15-ml Schlenk tube, 3.3 mg (0.005 mmol) of RuCl(R,R)—O-HT-Tsdpen), 0.67 ml (0.67 g, 5.0 mmol) of propiophenone, and 2.5 ml of a formic acid-triethylamine (5:2) azeotropic mixture were mixed, and the Schlenk tube was purged with nitrogen. Subsequently, the mixture was allowed to react for 24 hours at 60° C. An analysis of the reaction liquid was carried out by GC, and it was found that (R)-1-phenylpropan-1-ol with 93.7% ee was produced at a conversion rate of 99.7%.

Example 16

Asymmetric hydrogen transfer reaction of propiophenone using a complex RuCl(S,S)—O-HT-Msdpen)

In a 15-ml Schlenk tube, 2.9 mg (0.005 mmol) of RuCl(S,S)—O-HT-Msdpen), 0.67 ml (0.67 g, 5.0 mmol) of propiophenone, and 2.5 ml of a formic acid-triethylamine (5:2) azeotropic mixture were mixed, and the Schlenk tube was purged with nitrogen. Subsequently, the mixture was allowed to react for 24 hours at 60° C. An analysis of the reaction liquid was carried out by GC, and it was found that (S)-1-phenylpropan-1-ol with 92.1% ee was produced at a conversion rate of 95.9%.

Reference Example 1

Asymmetric hydrogen transfer reaction of propiophenone using a known complex RuCl((R,R)-Tsdpen)(mesitylene)

In a 15-ml Schlenk tube, 6.2 mg (0.01 mmol) of RuCl(R,R)-Tsdpen)(mesitylene), 0.67 ml (0.67 g, 5.0 mmol) of propiophenone, and 2.5 ml of a formic acid-triethylamine (5:2) azeotropic mixture were mixed, and the Schlenk tube was purged with nitrogen. Subsequently, the mixture was allowed to react for 24 hours at 60° C. An analysis of the reaction liquid was carried out by GC, and it was found that (R)-1-phenylpropan-1-ol with 93.0% ee was produced at a conversion rate of 52.3%.

Example 17

Asymmetric hydrogen transfer reactions of the ketones (1) to (14) presented in the following Tables 1 and 2 were respectively carried out in the same manner as in Example 15 using RuCl(R,R)—O-HT-Tsdpen), or in the same manner as in Example 10 using RuCl((S,S)—O-HT-Msdpen). Each reaction was carried out at the catalyst ratio (S/C) and temperature indicated in the tables, using a formic acid-triethylamine (5:2) azeotropic mixture as a hydrogen source in an amount such that the substrate concentration was 2 mol/L. After a lapse of a predetermined time, an analysis of the reaction liquid was carried out by GC, and thereby the conversion rate and the optical purity were determined.

Furthermore, as a comparison, the reaction results obtained in the same manner as in Reference Example 1 using the known complex RuCl(R,R)-Tsdpen)(mesitylene) are also presented in the right columns of the respective tables. In the tables that will be presented hereinafter, the abbreviation "conv." means the conversion rate of the substrate ketone; "selc." means the selectivity ratio to the target product; "% ee" represents the optical purity; and "S/C" represents the value of the ratio (mole number of substrate ketone/mole number of catalyst).

TABLE 1

| Substrate Ketone | RuCl(O-HT-Tsdpen) | RuCl(O-HT-Msdpen) | RuCl(Tsdpen) (mesitylene) |
|---|---|---|---|
| (1) Reaction Temperature: 60° C. | (S/C = 1000) 5 h; 100% conv. 93.6% ee | (S/C = 1000) 5 h; 99.4% conv. 93.2% ee | (S/C = 500) 24 h; 53.2% conv. 93.0% ee |
| (2) Reaction Temperature: 60° C. | (S/C = 1000) 5 h; 99.4% conv. 93.2% ee | (S/C = 1000) 5 h; 99.3% conv. 92.0% ee | (S/C = 500) 24 h; 20.8% conv. 86.6% ee |
| (3) Reaction Temperature: 60° C. | (S/C = 1000) 5 h; 93.6% conv. 83.6% ee | (S/C = 1000) 5 h; 97.8% conv. 96.5% ee | (S/C = 500) 24 h; 15.0% conv. 65.8% ee |

TABLE 1-continued

| Substrate Ketone | RuCl(O-HT-Tsdpen) | RuCl(O-HT-Msdpen) | RuCl(Tsdpen)(mesitylene) |
|---|---|---|---|
| 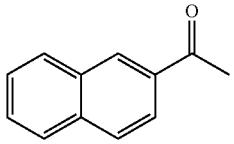<br>Reaction Temperature: 60° C.<br>(4) | (S/C = 1000)<br>5 h;<br>98.5% conv.<br>93.3% ee | (S/C = 1000)<br>5 h;<br>98.8% conv.<br>90.5% ee | (S/C = 500)<br>24 h;<br>28.1% conv.<br>90.6% ee |
| 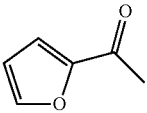<br>Reaction Temperature: 60° C.<br>(5) | (S/C = 1000)<br>5 h;<br>100% conv.<br>97.7% ee | (S/C = 1000)<br>5 h;<br>99.5% conv.<br>96.8% ee | (S/C = 500)<br>24 h;<br>25.0% conv.<br>94.5% ee |
| 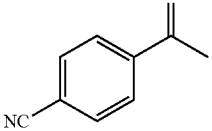<br>Reaction Temperature: 40° C.<br>(6) | (S/C = 1000)<br>24 h;<br>98.5% conv.<br>86.2% ee | (S/C = 1000)<br>24 h;<br>98.6% conv.<br>87.0% ee | (S/C = 500)<br>24 h;<br>59.0% conv.<br>88.0% ee |
| 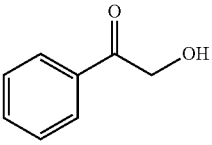<br>Reaction Temperature: 40° C.<br>(7) | (S/C = 1000)<br>5 h;<br>97.6% conv.<br>96.0% ee | (S/C = 1000)<br>5 h;<br>97.1% conv.<br>96.1% ee | (S/C = 500)<br>5 h;<br>3.8% conv.<br>0% ee |
| 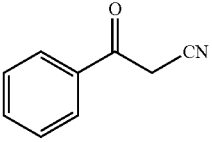<br>Reaction Temperature: 40° C.<br>(8) | (S/C = 1000)<br>5 h;<br>100% conv.<br>94.7% ee | (S/C = 1000)<br>5 h;<br>100% conv.<br>94.9% ee | (S/C = 500)<br>5 h;<br>65.0% conv.<br>96.2% ee |

TABLE 2

| Substrate Ketone | RuCl(O-HT-Tsdpen) | RuCl(O-HT-Msdpen) | RuCl(Tsdpen)(mesitylene) |
|---|---|---|---|
| 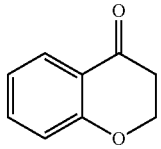<br>Reaction Temperature: 60° C.<br>(9) | (S/C = 1000)<br>5 h;<br>99.0% conv.<br>>99.9% ee | (S/C = 1000)<br>5 h;<br>99.4% conv.<br>99.8% ee | (S/C = 500)<br>24 h;<br>99.0% conv.<br>98.5% ee |
| 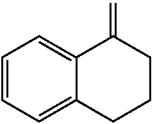<br>Reaction Temperature: 60° C.<br>(10) | (S/C = 1000)<br>5 h;<br>99.1% conv.<br>99.8% ee | (S/C = 1000)<br>5 h;<br>98.5% conv.<br>99.5% ee | (S/C = 500)<br>24 h;<br>61.9% conv.<br>97.8% ee |
| 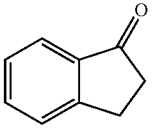<br>Reaction Temperature: 60° C.<br>(11) | (S/C = 1000)<br>5 h;<br>97.1% conv.<br>98.4% ee | (S/C = 1000)<br>5 h;<br>96.5% conv.<br>98.5% ee | (S/C = 500)<br>24 h;<br>17.4% conv.<br>90.1% ee |
| 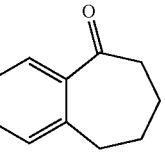<br>Reaction Temperature: 60° C.<br>(12) | (S/C = 1000)<br>24 h;<br>77.1% conv.<br>94.8% ee | (S/C = 1000)<br>24 h;<br>69.0% conv.<br>96.7% ee | (S/C = 500)<br>24 h;<br>1.9% conv.<br>51.5% ee |
| 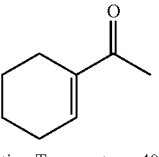<br>Reaction Temperature: 40° C.<br>(13) | (S/C = 500)<br>24 h;<br>71.3% conv.<br>(96.0% selc.)<br>63.0% ee | (S/C = 500)<br>24 h;<br>71.1% conv.<br>(95.3% selc.)<br>63.7% ee | (S/C = 200)<br>24 h;<br>38.3% conv.<br>(93.7% selc.)<br>52.3% ee |
| 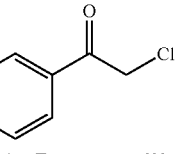<br>Reaction Temperature: 60° C.<br>(14) | (S/C = 1000)<br>5 h;<br>100% conv.<br>(>95% selc.)<br>97.3% ee | (S/C = 1000)<br>5 h;<br>100% conv.<br>(>95% selc.)<br>96.4% ee | (S/C = 500)<br>5 h;<br>97.7% conv.<br>(66% selc.)<br>90.9% ee |

The leftmost columns of Table 1 and Table 2 indicate the kind of ketones used as the substrate, and the next right columns indicate the results obtained when the complex RuCl((R,R)—O-HT-Tsdpen) of the present invention was used. The next right columns indicate the results obtained when the complex RuCl(S,S)—O-HT-Msdpen) of the present invention was used, and the rightmost columns indicate the results obtained when the known complex RuCl((R,R)-Tsdpen)(mesitylene) was used as a Comparative Example.

As such, the ruthenium complexes of the present invention having a heteroatom introduced into the chain-like moiety exhibit very high activities and selectivities, and the ruthenium complexes can produce optically active cyclic alcohols by reducing cyclic ketones, such as the ketones (9) to (12) which could not be hitherto efficiently reduced with hydrogenation catalysts or the like, or can produce optically active diols by reducing ketones having a hydroxyl group, such as the ketone (7). Similarly, the ruthenium complexes can produce optically active alcohols having a halogen substituent by hydrogenating ketones having a halogen substituent (particularly, ketones having a halogen substituent at the α-position), such as the ketone (14), which are unstable to bases and are therefore not easily reducible with conventional hydrogenation catalysts or the like. Thus, the ruthenium complexes according to the present invention are highly useful.

Example 18

Asymmetric Hydrogen Transfer Reaction of Benzil Using Complex RuCl(R,R)—O-HT-Tsdpen) (S/C=2000)

Benzil was asymmetrically reduced according to the following reaction formula.

[Chem. 19]

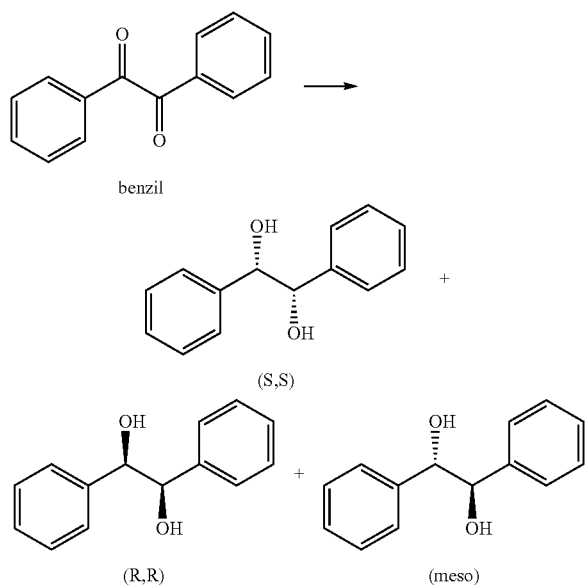

In a 50-ml Schlenk tube, 3.5 mg (0.005 mmol) of RuCl((R,R)—O-HT-Tsdpen), 2.1 g (10 mmol) of benzil, 5 ml of a formic acid-triethylamine (5:2) azeotropic mixture, and 10 ml of DMF were mixed, and the Schlenk tube was purged with nitrogen. Subsequently, the mixture was allowed to react for 5 hours at 60° C. An analysis of the reaction liquid was carried out by GC and HPLC, and it was found that hydrobenzoin was produced at the ratio of ((S,S) form: (R,R) form: meso form=88.1:0.9:11.0) at a conversion rate of 90.0%. The enantiomeric excess of the (S,S) form and the (R,R) form in this case is 98.0% ee.

Example 19

Asymmetric Hydrogen Transfer Reaction of (E)-N-(3,4-dihydronaphthalen-1(2H)-ylidene)-1-phenylmethanamine In a 50-ml Schlenk tube, 3.3 mg (0.005 mmol) (S/C=300) of RuCl(R,R)—O-HT-Tsdpen), 0.35 g (1.5 mmol) of the indicated imine, 3 ml of dichloromethane, and 0.75 ml of a formic acid-triethylamine (5:2) azeotropic mixture were mixed, and the mixture was allowed to react for 24 hours at 30° C. The yield and optical purity of the product were measured by a GC analysis, and as a result, optically active N-benzyl-1-(1,2,3,4-tetrahydronaphthyl)amine, which was the target amine, was obtained with a yield of 70.0% and an optical purity of 70% ee.

Example 20

Asymmetric Hydrogenation of 4-Chromanone

In a 50-ml autoclave, 3.3 mg (0.005 mmol, S/C=1000) of RuCl(R,R)—O-HT-Tsdpen) was placed, and the autoclave was purged with nitrogen. Subsequently, 0.74 g (5.0 mmol) of 4-chromanone and 4.4 ml of methanol were added thereto, and the pressure was raised with hydrogen up to 3.0 MPa. Subsequently, the mixture was stirred for 18 hours at 60° C. The reaction liquid was subjected to a GC analysis, and as a result, (R)-4-chromanol was obtained at a conversion rate of 98.6% with an optical purity of 99.1% ee.

Example 21

Asymmetric Hydrogenation of α-Tetralone

In a 50-ml autoclave, 3.3 mg (0.005 mmol, S/C=1000) of RuCl((R,R)—O-HT-Tsdpen) was placed, and the autoclave was purged with nitrogen. Subsequently, 0.73 g (5.0 mmol) of α-tetralone and 4.4 ml of methanol were added thereto, then hydrogen gas was charged to 3.0 MPa. Subsequently, the mixture was stirred for 20 hours at 60° C. The reaction liquid was subjected to a GC analysis, and as a result, (R)-1-tetralol was obtained at a conversion rate of 52.0% with an optical purity of 99.3% ee.

Example 22

Asymmetric hydrogenation of 1-indanone

In a 50-ml autoclave, 3.3 mg (0.005 mmol, S/C=1000) of RuCl(R,R)—O-HT-Tsdpen) was placed, and the autoclave was purged with nitrogen. Subsequently, 0.66 g (5.0 mmol) of 1-indanone and 4.4 ml of methanol were added thereto, then hydrogen gas was charged to 3.0 MPa. Subsequently, the mixture was stirred for 20 hours at 60° C. The reaction liquid was subjected to a GC analysis, and as a result, (R)-1-indanol was obtained at a conversion rate of 58.6% with an optical purity of 97.8% ee.

Example 23

The hydrogenation of methyl benzoate using RuCl ((R,R)—O-HT-Tsdpen)

In a 50-ml autoclave, 13.5 mg (0.020 mmol, S/C=50) of RuCl(R,R)—O-HT-Tsdpen) was placed, and the autoclave was purged with nitrogen. Subsequently, 1.8 ml of tetrahydrofuran and 0.14 g (1.0 mmol) of methyl benzoate, 0.2 ml (0.20 mmol) of the 1.0M tetrahydrofuran solution of potassium tert-Butoxide were added thereto, then hydrogen gas was charged to 5.0 MPa. Subsequently, the mixture was stirred for 15 hours at 60° C. The reaction liquid was subjected to a GC analysis, and as a result, benzyl alcohol was obtained at a conversion rate of 90.4% with an selectivity of 78.9%.

Reference Example 2

In order to investigate the effects of the heteroatom in the novel ruthenium-diamine complexes having a heteroatom introduced into the chain-like moiety that links the aromatic compound (arene) portion and the diamine moiety that are coordinated to ruthenium, which has been newly discovered in this invention, the following complex which does not have any heteroatom, and in which the chain-like moiety is composed only of carbon atoms, was separately synthesized, and a comparison of activity was made.

[Chem. 20]

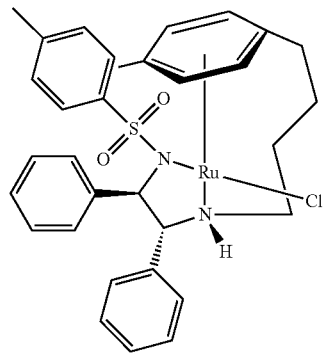

The complex was produced by making reference to the production method described in the Non-Patent Literature 5 (J. Am. Chem. Soc. 127 (2005), p. 7318). This newly produced complex will be hereinafter referred to as RuCl(p-Tol-$C_4$-teth-Tsdpen).

$^1$H-NMR(CDCl$_3$, 300 MHz) δ:

1.82-2.04 (m, 2H), 2.04-2.31 (m, 5H), 2.26 (s, 3H), 2.53 (s, 3H), 2.89-2.71 (m, 2H), 3.10-3.16 (m, 1H), 3.47-3.56 (m, 1H), 3.80 (dd, J=11.1, 12.1 Hz, 1H), 3.99 (d, J=11.1 Hz, 1H), 4.77 (m, 1H), 5.32 (d, J=5.5 Hz, 2H), 5.38 (d, J=6.3 Hz, 2H), 5.55 (d, J=6.3 Hz, 1H), 6.20 (d, J=5.5 Hz, 1H), 6.61 (d, J=7.2 Hz, 1H), 6.59-6.62 (m, 2H), 6.71-6.81 (m, 4H), 6.83-6.91 (m, 3H), 7.03-7.12 (m, 3H), 7.18 (d, J=8.4 Hz, 2H);

HRMS (ESI):

As $C_{32}H_{35}N_2O_2SRu$.

Calculated value: [M−Cl]$^+$ 613.1457.

Found value: 613.1473.

Example 24

In order to investigate the activities of the complex RuCl ((R,R)—O-HT-Tsdpen) having a heteroatom in the side chain moiety and of the complex RuCl(p-Tol-$C_4$-teth-Tsdpen) produced in Reference Example 2, in which the side chain moiety is composed only of carbon atoms, hydrogen transfer reactions of acetophenone were carried out at catalyst ratios such as indicated in the following table. The reactions were carried out at the catalyst ratios indicated in the following Table 3 and at 60° C., using a formic acid-triethylamine (5:2) azeotropic mixture as a hydrogen source in an amount such that the substrate concentration was 2 mol/L. After a lapse of a predetermined time, an analysis of the reaction liquids was carried out by GC, and thereby the conversion rate and the optical purity were determined.

The results are presented in the following Table 3.

TABLE 3

| Catalytic Ratio (S/C) | RuCl(O-HT-Tsdpen) | RuCl(p-Tol-$C_4$-teth-Tsdpen) |
|---|---|---|
| 1000 | (20 h) 99.0% conv. 96.3% ee | (20 h) 99.0% conv. 96.3% ee |
| 5000 | (24 h) 94.8% conv. 96.2% ee | (24 h) 94.6% conv. 96.3% ee |
| 10000 | (24 h) 71.5% conv. 96.1% ee | (24 h) 40.0% conv. 94.9% ee |
|  | (48 h) 91.5% conv. 96.2% ee | (48 h) 43.1% conv. 94.4% ee |
|  | (72 h) 95.2% conv. 96.2% ee | (72 h) — |
| 15000 | (24 h) 61.0% conv. 96.1% ee | (24 h) 6.5% conv. 79.7% ee |
|  | (48 h) 87.3% conv. 96.3% ee | (48 h) — |
|  | (72 h) 94.1% conv. 96.3% ee |  |

As such, the complex RuCl(O-HT-Tsdpen) having a heteroatom in the side chain moiety, and the complex RuCl(p-Tol-$C_4$-teth-Tsdpen) in which the side chain moiety is composed only of carbon atoms, both exhibit high activities in the acetophenone reduction reaction as compared with the conventional hydrogen transfer type complexes, and both of the complexes gave equally satisfactory results in the reactions at catalyst ratios of up to S/C=5000. However, when the catalyst ratio was increased to S/C=10,000, the reaction carried out using the complex RuCl(O-HT-Tsdpen) of the present invention was almost completed, but in the reaction using the complex RuCl(p-Tol-$C_4$-teth-Tsdpen), the conversion rate was only around 40%, while the reaction was stopped due to deactivation of the catalyst. Furthermore, when the catalyst ratio was increased to S/C=15,000, the reaction carried out using the complex RuCl(O-HT-Tsdpen) of the present invention was likewise almost completed, but the reaction hardly proceeded when the complex RuCl(p-Tol-$C_4$-teth-Tsdpen) was used. Therefore, when a comparison was made between these two complexes which respectively have an equal length of the side chain that links the skeleton on the arene or links the arene and diamine portions, but different elements constituting the side chain, such as oxygen atoms and carbon atoms, it was found that the complex RuCl(O-HT-Tsdpen) of the present invention having an oxygen atom among the atoms constituting the side chain exhibits a very high catalytic activity even when used in a very small amount.

Example 25

Production of Ru(BF$_4$)((R,R)—O-HT-Tsdpen)

In a 150-ml Schlenk tube, 0.52 g (0.8 mmol, 1 eq) of RuCl((R,R)—O-HT-Tsdpen), 0.187 g (0.96 mmol, 1.2 eq) of AgBF$_4$, 15 ml of dichloromethane, and 15 ml of methanol were mixed, and the mixture was stirred for one hour at room temperature. The reaction solution was filtered through Celite, and the filtrate was dried to solid. Thus, 0.55 g (98% yield) of the desired complex, RuBF$_4$((R,R)—O-HT-Tsdpen), was obtained.

$^1$H-NMR(CD$_3$OD, 300 MHz) δ:

2.12 (s, 3H), 2.46 (s, 3H), 3.35-3.60 (m, 4H), 3.60-3.80 (m, 1H), 3.95-4.10 (m, 3H), 4.70-4.80 (m, 1H), 5.84 (d, 1H), 5.89 (d, 1H), 5.99 (d, 1H), 6.20 (d, 1H), 6.46-7.50 (m, 14H)

HRMS (ESI):

As $C_{31}H_{33}BF_4N_2O_3RuS$.

Calculated value: [M−BF$_4$]$^+$ 615.1250.

Found value: 615.1271.

Example 26

Production of Ru(OTf)((R,R)—O-HT-Tsdpen)

In a 150-ml Schlenk tube, 0.52 g (0.8 mmol, 1 eq) of RuCl(R,R)—O-HT-Tsdpen), 0.247 g (0.96 mmol, 1.2 eq) of AgOTf, 15 ml of dichloromethane, and 15 ml of methanol were mixed, and the mixture was stirred for one hour at room temperature. The reaction solution was filtered through Celite, and the filtrate was dried to solid. Thus, 0.59 g (96% yield) of the desired complex, RuOTf(R,R)—O-HT-Tsdpen), was obtained.

$^1$H-NMR(CD$_3$OD 300 MHz) δ:
2.13 (s, 3H), 2.47 (s, 3H), 3.35-3.60 (m, 4H), 3.60-3.80 (m, 1H), 3.95-4.10 (m, 3H), 4.70-4.80 (m, 1H), 5.84 (d, 1H), 5.89 (d, 1H), 5.99 (d, 1H), 6.20 (d, 1H), 6.46-7.50 (m, 14H)
HRMS (ESI):
As C$_{32}$H$_{33}$F$_3$N$_2$O$_6$RuS$_2$.
Calculated value: Positive side [M−TfO]$^+$ 615.1250.
Negative side [TfO]$^-$ 148.9526.
Found value: Positive side [M−TfO]$^+$ 615.1258.
Negative side [TfO]$^-$ 148.9521.

Example 27

Production of Ru(SbF$_6$)((R,R)—O-HT-Tsdpen)

In a 150-ml Schlenk tube, 0.52 g (0.8 mmol, 1 eq) of RuCl((R,R)—O-HT-Tsdpen), 0.330 g (0.96 mmol, 1.2 eq) of AgSbF$_6$, 15 ml of dichloromethane, and 15 ml of methanol were mixed, and the mixture was stirred for one hour at room temperature. The reaction solution was filtered through Celite, and the filtrate was dried to solid. Thus, 0.65 g (95% yield) of the desired complex, RuSbF$_6$((R,R)—O-HT-Tsdpen), was obtained.

$^1$H-NMR(CD$_3$OD, 300 MHz) δ:
2.16 (s, 3H), 2.42 (s, 3H), 3.30-3.60 (m, 4H), 3.60-3.80 (m, 1H), 4.00-4.15 (m, 3H), 4.70-4.80 (m, 1H), 5.83 (d, 1H), 5.91 (d, 1H), 5.97 (d, 1H), 6.19 (d, 1H), 6.48-7.25 (m, 14H)
HRMS (ESI):
As C$_{31}$H$_{33}$F$_6$N$_2$O$_3$RuSSb.
Calculated value: [M−SbF$_6$]$^+$ 615.1250.
Found value: 615.1251.

Example 28

Production of Ru(CF$_3$COO)((R,R)—O-HT-Tsdpen)

In a 150-ml Schlenk tube, 0.52 g (0.8 mmol, 1 eq) of RuCl((R,R)—O-HT-Tsdpen), 0.212 g (0.96 mmol, 1.2 eq) of CF$_3$COOAg, 15 ml of dichloromethane, and 15 ml of methanol were mixed, and the mixture was stirred for one hour at room temperature. The reaction solution was filtered through Celite, and the filtrate was dried to solid. Thus, 0.58 g (99% yield) of the desired complex, Ru(CF$_3$COO)((R,R)—O-HT-Tsdpen), was obtained.
HRMS (ESI):
As C$_{33}$H$_{33}$F$_3$N$_2$O$_6$RuS.
Calculated value: [M−CF$_3$COO]$^+$ 615.1250.
Found value: 615.1243.

Example 29

Production of Ru(CH$_3$COO)((R,R)—O-HT-Tsdpen)

In a 150-ml Schlenk tube, 0.52 g (0.8 mmol, 1 eq) of RuCl((R,R)—O-HT-Tsdpen), 0.16 g (0.96 mmol, 1.2 eq) of CH$_3$COOAg, 15 ml of dichloromethane, and 15 ml of methanol were mixed, and the mixture was stirred for one hour at room temperature. The reaction solution was filtered through Celite, and the filtrate was dried to solid. Thus, 0.50 g (92% yield) of the desired complex, Ru(CH$_3$COO)((R,R)—O-HT-Tsdpen), was obtained.

$^1$H-NMR(d$^6$-DMSO, 300 MHz) δ:
1.89 (s, 3H), 2.18 (s, 3H), 2.26 (s, 3H), 3.00-4.00 (m, 4H), 3.85 (d, 1H), 4.03 (t, 1H), 4.62 (d, 1H), 4.85 (d, 1H), 4.03 (t, 1H), 5.53 (m, 2H), 5.97 (m, 2H), 6.48-7.60 (m, 14H), 10.07 (m, 1H),
HRMS (ESI):
As C$_{33}$H$_{36}$N$_2$O$_5$RuS.
Calculated value: [M−CH$_3$COO]$^+$ 615.1250.
Found value: 615.1240.

Example 30

Production of Ru(B(C$_6$F$_5$)$_4$)((R,R)—O-HT-Tsdpen)

In a 150-ml Schlenk tube, 0.40 g (0.61 mmol, 1 eq) of RuCl(R,R)—O-HT-Tsdpen), 0.5 g (0.74 mmol, 1.2 eq) of LiB(C$_6$F$_5$)$_4$, 11 ml of dichloromethane, and 11 ml of methanol were mixed, and the mixture was stirred for one hour at room temperature. The reaction solution was filtered through Celite, and the filtrate was dried to solid. Thus, 0.74 g (93% yield) of the desired complex, Ru(B(C$_6$F$_5$)$_4$)((R,R)—O-HT-Tsdpen), was obtained.

$^1$H-NMR(CD$_3$OD, 300 MHz) δ:
2.15 (s, 3H), 2.39 (s, 3H), 3.10-3.23 (m, 2H), 3.40-3.58 (m, 2H), 3.70-4.00 (m, 2H), 3.90 (t, 1H), 4.15 (d, 1H), 4.62 (m, 1H), 5.60-5.95 (m, 4H), 6.52-7.25 (m, 14H) $^{19}$F-NMR (CD$_3$OD) δ:
−168.8, −164.9, −133.0
HRMS (ESI):
As C$_{55}$H$_{33}$BF$_{20}$N$_2$O$_3$RuS.
Calculated value: Positive side [M−B(C$_6$F$_5$)$_4$]$^+$ 615.1250.
Negative side [B(C$_6$F$_5$)$_4$]$^-$ 678.9776.
Found value: Positive side [M−B(C$_6$F$_5$)$_4$]$^+$ 615.1254.
Negative side [B(C$_6$F$_5$)$_4$]$^-$ 678.9774.

Example 31

Asymmetric Hydrogen Transfer Reaction of Acetophenone Using Complex Ru(BF$_4$)((R,R)—O-HT-Tsdpen) (S/C=1000)

In 15-ml Schlenk tube, 3.5 mg (0.005 mmol) of the complex Ru(BF$_4$)((R,R)—O-HT-Tsdpen) produced in Example 25 as described above, 0.58 ml (0.6 g, 5 mmol) of acetophenone, and 2.5 ml of a formic acid-triethylamine (5:2) azeotropic mixture were mixed, and the Schlenk tube was purged with nitrogen. Subsequently, the mixture was allowed to react for 5 hours at 60° C. An analysis of the reaction liquid was carried out by GC, and it was found that (R)-1-phenylethanol with 96.2% ee was produced at a conversion rate of 96.5%.

Example 32

Asymmetric Hydrogenation Reaction of 2-Methylquinoline Using Complex Ru(BF$_4$)((R,R)—O-HT-Tsdpen)

In a 100-ml autoclave, 17.5 mg (0.025 mmol) of Ru(BF$_4$)((R,R)—O-HT-Tsdpen) was placed, and the autoclave was purged with nitrogen. Subsequently, 0.34 ml (0.36 g, 2.5 mmol) of 2-methylquinoline and 1.4 ml of HFIP (hexafluoro-2-propanol) were added thereto, then hydrogen gas was charged to 5.0 MPa. Subsequently, the mixture was stirred for 19 hours at 40° C. The reaction liquid was subjected to a GC analysis, and as a result, it was found that 1,2,3,4-tetrahydroquinaldine, which is a reduced form, was produced at a conversion rate of 93.8%, with an optical purity of 86% ee.

Example 33

[Chem. 21]

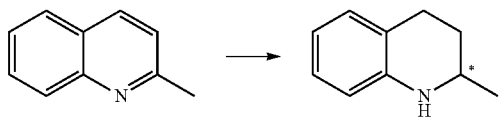

Asymmetric hydrogenation reactions were carried out in the same manner as in Example 32, by respectively using Ru(BF$_4$)((R,R)—O-HT-Tsdpen), Ru(OTf)((R,R)—O-HT-Tsdpen), Ru(SbF$_6$)((R,R)—O-HT-Tsdpen), Ru(CF$_3$COO)((R,R)—O-HT-Tsdpen), Ru(CH$_3$COO)((R,R)—O-HT-Tsd-pen) or Ru(B(C$_6$F$_5$)$_4$)((R,R)—O-HT-Tsdpen) as the catalyst, and using HFIP or methanol as the solvent. 2-Methylquinoline was used as the substrate for the reactions, and the reactions were respectively carried out for 19 hours. The results are presented in the following Table 4.

TABLE 4

| Catalyst (S/C = 100) | Solvent | Conversion rate (% conv.) | Assymetric yield (% ee) |
|---|---|---|---|
| Ru(BF$_4$)(O-HT-Tsdpen) | HFIP | 93.8 | 86 |
| | MeOH | 95.7 | 58 |
| Ru(OTf)(O-HT-Tsdpen) | HFIP | 98.1 | 90 |
| | MeOH | 84.3 | 42 |
| Ru(SbF$_6$)(O-HT-Tsdpen) | HFIP | 97.2 | 86 |
| | MeOH | 85.8 | 46 |
| Ru(CF$_3$COO)(O-HT-Tsdpen) | HFIP | 98.4 | 90 |
| | MeOH | 79.1 | 35 |
| Ru(CH$_3$COO)(O-HT-Tsdpen) | HFIP | 98.8 | 91 |
| | MeOH | 56.2 | 16 |
| Ru(B(C$_6$F$_5$)$_4$)(O-HT-Tsdpen) | HFIP | 92.1 | 90 |
| | MeOH | 51.4 | 28 |

Example 34

Asymmetrichydrogenation Reaction of 2-Methylquinoxaline Using Complex Ru(BF$_4$)((R,R)—O-HT-Tsdpen)

In a 100-ml autoclave, 17.5 mg (0.025 mmol) of Ru(BF$_4$)((R,R)—O-HT-Tsdpen) was placed, and the autoclave was purged with nitrogen. Subsequently, 0.32 ml (0.36 g, 2.5 mmol) of 2-methylquinoxaline and 1.4 ml of HFIP (hexafluoro-2-propanol) were added thereto, then hydrogen gas was charged to 5.0 MPa. Subsequently, the mixture was stirred for 20 hours at 50° C. The reaction liquid was subjected to a GC analysis, and as a result, it was found that 2-methyl-1,2,3,4-tetrahydroquinoxaline, which is a reduced form, was produced at a conversion rate of 68.5%, with an optical purity of 48% ee.

Example 35

[Chem. 22]

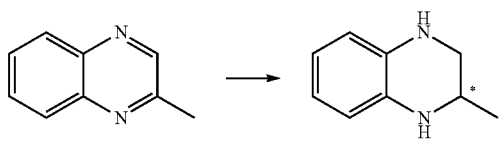

Asymmetrichydrogenation reactions were carried out in the same manner as in Example 34, by respectively using Ru(BF$_4$)((R,R)—O-HT-Tsdpen), Ru(OTf)((R,R)—O-HT-Tsdpen), Ru(SbF$_6$)((R,R)—O-HT-Tsdpen) as the catalyst, in the BEEP solvent. 2-Methylquinoxaline was used as the substrate for the reactions, and the reactions were respectively carried out for 20 hours. The results are presented in the following Table 5.

TABLE 5

| Catalyst (S/C = 100) | Solvent | Conversion rate (% conv.) | Assymetric yield (% ee) |
|---|---|---|---|
| Ru(BF$_4$)(O-HT-Tsdpen) | HFIP | 68.5 | 48 |
| Ru(OTf)(O-HT-Tsdpen) | HFIP | 66.0 | 46 |
| Ru(SbF$_6$)(O-HT-Tsdpen) | HFIP | 65.2 | 46 |

Example 36

Production of 2-((4-methylcyclohexa-1,4-dienyl)methoxy)ethanol and 2((5-methylcyclohexa-1,4-dienyl)methoxy)ethanol

[Chem. 23]

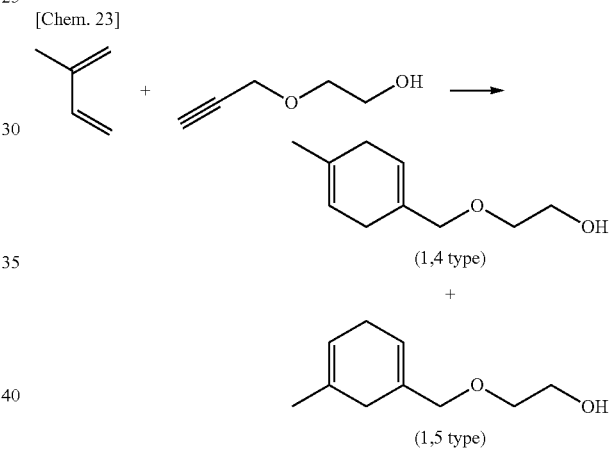

7.74 g (0.019 mol) of 1,2-bis(diphenylphosphino)ethane, 4.05 g (0.019 mol) of cobalt bromide, 11.82 g (0.037 mol) of zinc iodide, and 2.42 g (0.037 mol) of zinc were added to 460 ml of THF, and the solution was stirred for 15 minutes at 70° C. The solution was cooled to room temperature, and 74.89 g (1.10 mol) of isoprene was added thereto. Subsequently, 92.70 g (0.93 mol) of alkynyl alcohol was slowly added dropwise to the mixture in a water bath. The resulting mixture was stirred for one hour at 35° C., and then the solvent was distilled off under a reduced pressure. To the residue thus obtained, 460 ml of toluene and 460 ml of water were added (stirred for 10 minutes, and left to stand for 10 minutes). The mixture was filtered through Celite in a nitrogen atmosphere, and then the organic layer of solution thus obtained was separated. The solvent was distilled off under reduced pressure, and the crude product thus obtained was purified by Claisen distillation (101° C.-113° C., at 3 torr). Thus, 106.6 g of diene alcohol was obtained as a colorless oil. Yield 68.5% (1,4-type/1,5-type=91/9).

$^1$H-NMR(CDCl$_3$, 300 MHz) δ:

1.68 (s, 3H), 2.31 (brs, 1H), 2.64 (brs, 4H), 3.48-3.52 (m, 2H), 3.70-3.75 (m, 2H), 3.93 (s, 2H), 5.43-5.45 (m, 1H), 5.70-5.71 (m, 1H);

HRMS (ESI):

As $C_{10}H_{16}O_2$.

Calculated value: $[M+H]^+$ 167.1430.

Found value: 167.1432.

Example 37

Production of 2-((4-methylcyclohexa-1,4-dienyl)methoxy)ethyl 4-methylbenzenesulfonate and 2-((5-methylcyclohexa-1,4-dienyl)methoxy)ethyl 4-methylbenzenesulfonate

[Chem. 24]

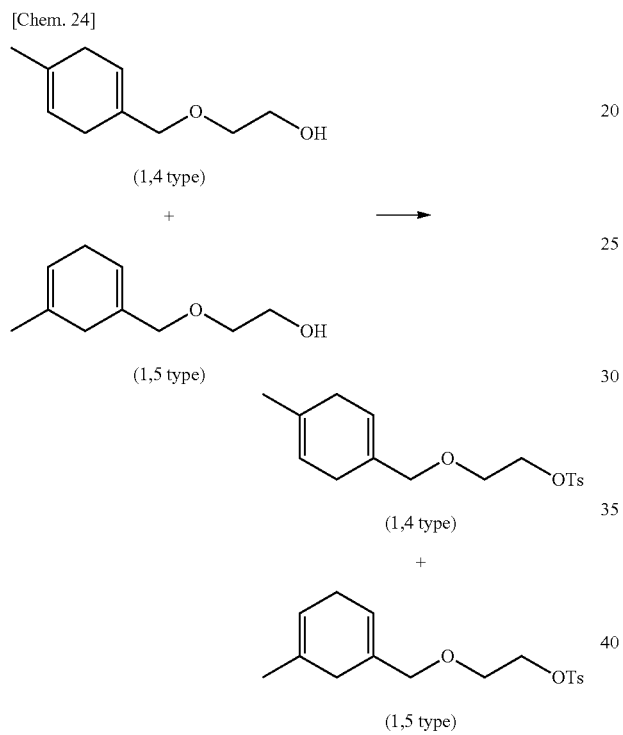

100.00 g (0.59 mol) of the diene alcohol obtained in Example 36, 90.29 g (0.89 mol) of triethylamine, and 73.20 g (0.89 mol) of 1-methylimidazole were dissolved in 400 ml of toluene. In an ice bath, a toluene solution (400 ml) of 130.33 g (0.68 mol) of p-toluenesulfonyl chloride was slowly added dropwise to the solution, and then the resulting mixture was stirred for one hour at room temperature. Water was added thereto, and the organic layer was separated. The obtained organic layer was washed sequentially with 15% sulfuric acid, water, and a saturated aqueous sodium hydrogen carbonate. The solvent was distilled off under reduced pressure, and thus 188.01 g of the desired tosylate was obtained as a colorless oil. Yield 98.1% (1,4-type/1,5-type=91/9).

$^1$H-NMR(CDCl$_3$, 300 MHz) δ:

1.67 (s, 3H), 2.44 (s, 3H), 2.58 (brs, 4H), 3.58-3.55 (m, 2H), 3.84 (s, 2H), 4.18-4.14 (m, 2H), 5.41-5.40 (m, 1H), 5.64-5.63 (m, 1H), 7.33 (d, J=8.3 Hz, 1H), 7.80 (d, J=8.3 Hz, 1H);

HRMS (ESI):

As $C_{17}H_{22}O_4S$.

Calculated value: $[M+H]^+$ 323.1312.

Found value: 323.1325.

Example 38

Production of 4-methyl-N-((1R,2R)-2-(2-((4-methylcyclohexa-1,4-dienyl)methoxy)ethylamino)-1,2-diphenylethyl)benzenesulfonamide hydrochloride and 4-methyl-N-((1R,2R)-2-(2-((5-methylcyclohexa-1,4-dienyl)methoxy)ethylamino)-1,2-diphenylethyl)benzenesulfonamide hydrochloride

[Chem. 25]

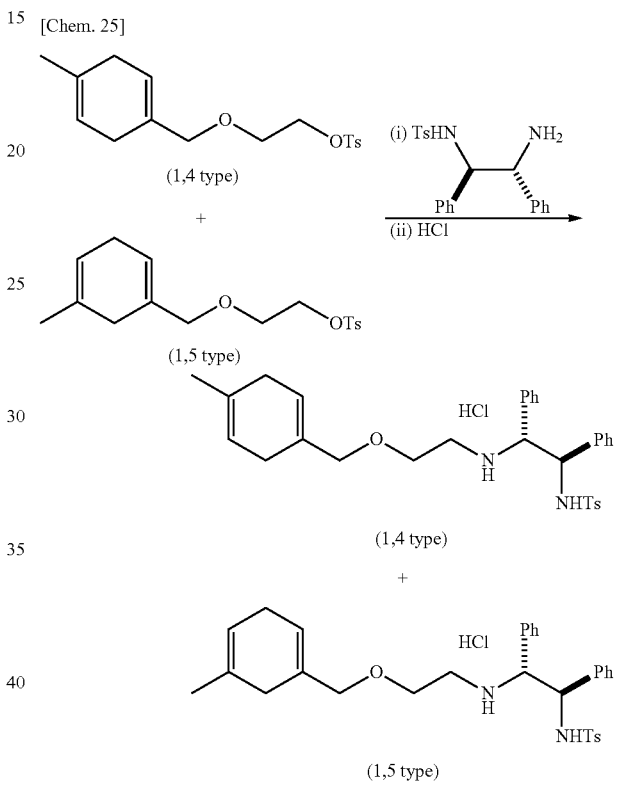

2.2 g (6.9 mmol) of the tosylate obtained in Example 37 was dissolved in 10 ml of toluene, and 0.90 g (6.9 mmol) of DIPEA and 2.53 g (6.9 mmol) of (R,R)-TsDPEN were added to the solution. The resulting mixture was stirred for 27 hours at 135° C. Water was added thereto, and the organic layer was separated. The obtained organic layer was washed with water, then 20% hydrochloric acid was added thereto. The resulting mixture was stirred for one hour at room temperature, and then was precipitated under ice cooling. Crystals precipitated therefrom were collected by filtration, and thus 3.14 g of the desired diamine hydrochloride was obtained as a white solid. Yield 82.3%.

$^1$H-NMR(CDCl$_3$, 300 MHz) δ:

1.43-1.80 (m, 6H), 2.32 (s, 3H), 2.42-2.70 (m, 2H), 3.40-3.55 (m, 2H), 3.70-3.85 (m, 2H), 3.77 (d, 1H), 4.30 (m, 1H), 4.45 (d, 1H), 6.93-7.38 (m, 14H);

HRMS (ESI):

As $C_{31}H_{37}N_2O_3S$.

Calculated value: $[M-Cl]^+$ 517.2519.

Found value: 517.2523.

Example 39

Production of RuCl((R,R)—O-HT-Tsdpen)

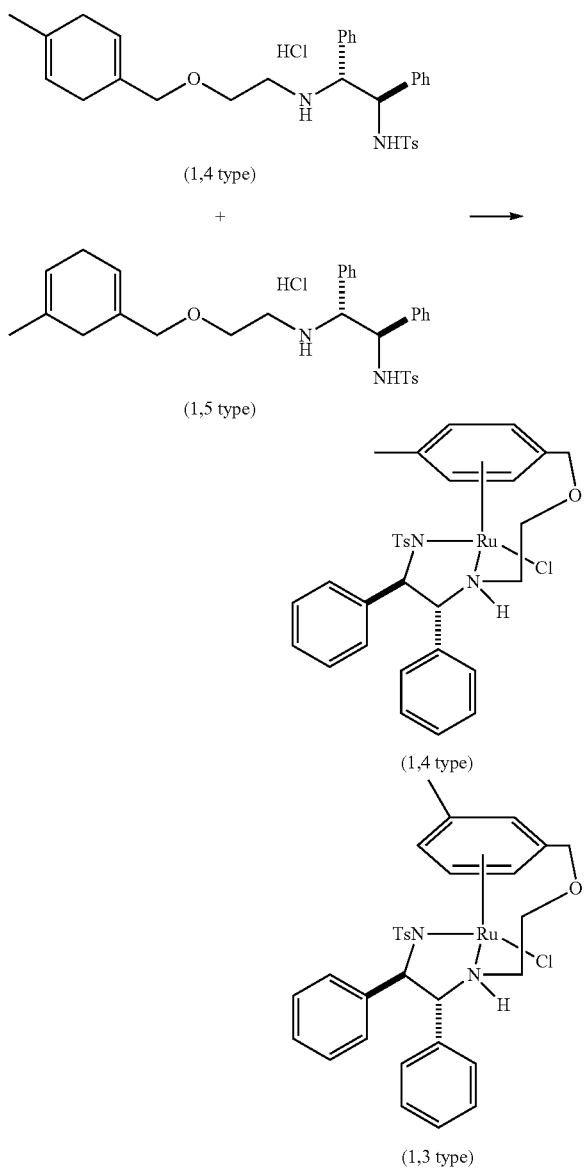

25.15 g (45.20 mmol) of the diamine hydrochloride produced in Example 38 was dissolved in 375 ml of 3-methoxypropanol and 75 ml of water. 10.74 g (41.09 mmol) of ruthenium trichloride trihydrate and 3.45 g (41.09 mmol) of sodium hydrogen carbonate were added to the solution, and the resulting mixture was stirred for 45 minutes at 120° C. 3-methoxypropanol was recovered, and then 425 ml of MIBK and 16.63 g (164.4 mmol) of triethylamine were added to the reaction liquid, and the mixture was stirred for one hour at 60° C. Heptane was added to the residue which washed by 0.3 M hydrochloric acid, and the residue was subjected to crystallization. And thus 22.26 g of the desired Ru complex was obtained. Yield 83.3%.

$^1$H-NMR(CDCl$_3$, 500 MHz) δ:
2.26 (s, 3H), 2.52 (s, 3H), 3.14-3.10 (m, 1H), 3.60-3.56 (m, 1H), 3.98-3.91 (m, 4H), 4.58-4.45 (m, 2H), 4.96-4.92 (m, 1H), 5.46 (brd, J=3.6 Hz, 1H), 5.62 (d, J=6.3 Hz, 1H), 5.75 (d, J=6.3 Hz, 1H), 6.05 (brd, J=3.6 Hz, 1H), 6.60 (d, J=7.3 Hz, 2H), 6.75-6.69 (m, 4H), 7.21 (d, J=8.0 Hz, 2H), 6.84 (d, J=7.3 Hz, 1H), 6.88 (d, J=8.0 Hz, 2H), 7.17-7.08 (m, 4H);

HRMS (ESI):
As C$_{31}$H$_{34}$ClN$_2$O$_3$RuS.
Calculated value: [M+H]$^+$ 651.1057.
Found value: 651.1008.

Example 40

Production of RuCl((R,R)—O-HT-Tsdpen)-dimer

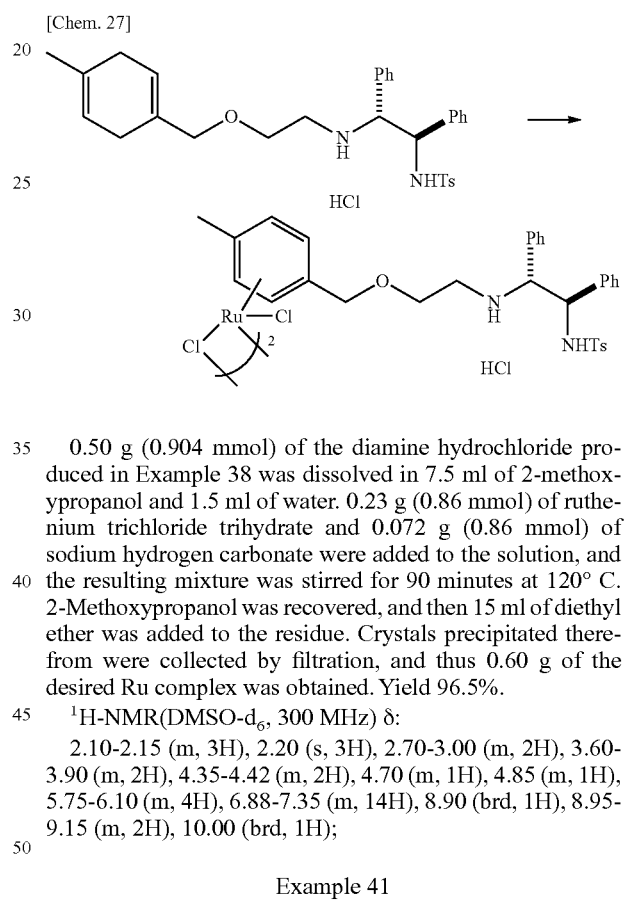

0.50 g (0.904 mmol) of the diamine hydrochloride produced in Example 38 was dissolved in 7.5 ml of 2-methoxypropanol and 1.5 ml of water. 0.23 g (0.86 mmol) of ruthenium trichloride trihydrate and 0.072 g (0.86 mmol) of sodium hydrogen carbonate were added to the solution, and the resulting mixture was stirred for 90 minutes at 120° C. 2-Methoxypropanol was recovered, and then 15 ml of diethyl ether was added to the residue. Crystals precipitated therefrom were collected by filtration, and thus 0.60 g of the desired Ru complex was obtained. Yield 96.5%.

$^1$H-NMR(DMSO-d$_6$, 300 MHz) δ:
2.10-2.15 (m, 3H), 2.20 (s, 3H), 2.70-3.00 (m, 2H), 3.60-3.90 (m, 2H), 4.35-4.42 (m, 2H), 4.70 (m, 1H), 4.85 (m, 1H), 5.75-6.10 (m, 4H), 6.88-7.35 (m, 14H), 8.90 (brd, 1H), 8.95-9.15 (m, 2H), 10.00 (brd, 1H);

Example 41

Asymmetric Hydrogen Transfer Reaction of Acetophenone Using Complex RuCl((R,R)—O-HT-Tsdpen)-dimer (S/C=1000)

In a 50-ml Schlenk tube, 3.6 mg (0.005 mmol) of the complex RuCl(R,R)—O-HT-Tsdpen)-dimer produced in Example 40 as described above, 0.58 ml (0.60 g, 5 mmol) of acetophenone, and 2.5 ml of a formic acid-triethylamine (5:2) azeotropic mixture were mixed, and the Schlenk tube was purged with nitrogen. Subsequently, the mixture was allowed to react for 5 hours at 60° C. An analysis of the reaction liquid was carried out by GC, and it was found that (R)-1-phenylethanol with 96.2% ee was produced at a conversion rate of 97.5%.

Example 42

Production of N-((1R,2R)-2-(2-((4-methylcyclohexa-1,4-dienyl)methoxy)ethylamino)-1,2-diphenylethyl)-2-(trifluoro methyl)benzenesulfonamide hydrochloride

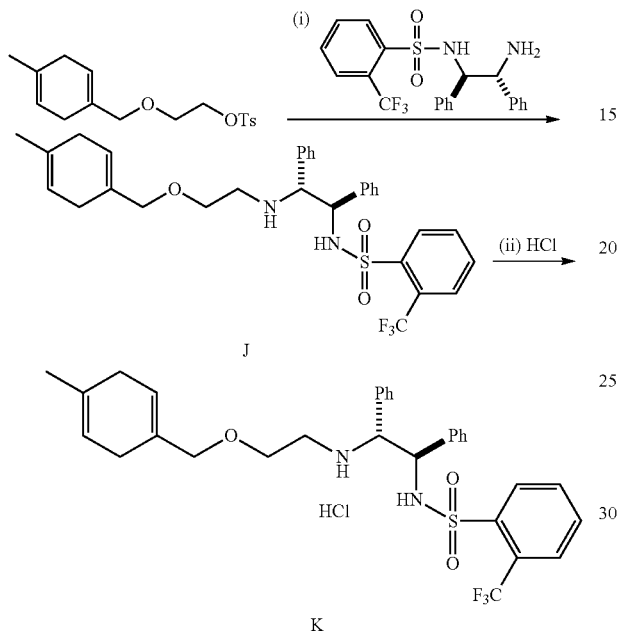

8.07 g (26.1 mmol) of the tosylate obtained in Example 37 was dissolved in 31.6 ml of toluene, and 3.38 g (26.2 mmol) of DIPEA, 10.00 g (23.8 mmol) of (R,R)-o-TFTsDPEN, and 4.34 g (26.2 mmol) of potassium iodide were added to the solution. The resulting mixture was stirred for 6 hours at 135° C. The reaction liquid was concentrated, and was purified by silica gel column chromatography. Thus, 10.1 g of diamine J was obtained. Yield 74.5%. Subsequently, 110 ml of dichloromethane and 65.3 ml of an HCl-methanol solution (1 N) were added to 10.1 g (17.7 mmol) of the diamine J, and the resulting mixture was stirred for 0.5 hours. Subsequently, the solvent was removed, and thus 11.1 g of the desired diamine hydrochloride K was obtained. Yield 93.9%.

$^1$H-NMR(DMSO-$d_6$, 300 MHz) δ:

1.62 (m, 3H), 2.60 (s, 3H), 2.78-3.12 (m, 2H), 3.52-3.70 (m, 2H), 3.86 (s, 2H), 4.75 (m, 1H), 4.92 (m, 1H), 5.40 (m, 1H), 5.68 (m, 1H), 6.75-7.35 (m, 10H), 7.40 (t, 1H), 7.50 (t, 1H), 7.60 (d, 1H), 7.75 (d, 1H), 8.90 (m, 1H), 8.98 (brd, 1H), 9.92 (brd, 1H);

$^{19}$F-NMR(DMSO-$d_6$) δ:

−57.16

HRMS (ESI):

As $C_{31}H_{33}N_2O_3F_3S\cdot HCl$.

Calculated value: $[M-Cl]^+$ 571.2237.

Found value: 571.2244.

Example 43

Production of RuCl(R,R)—O-HT-o-TFTsdpen)

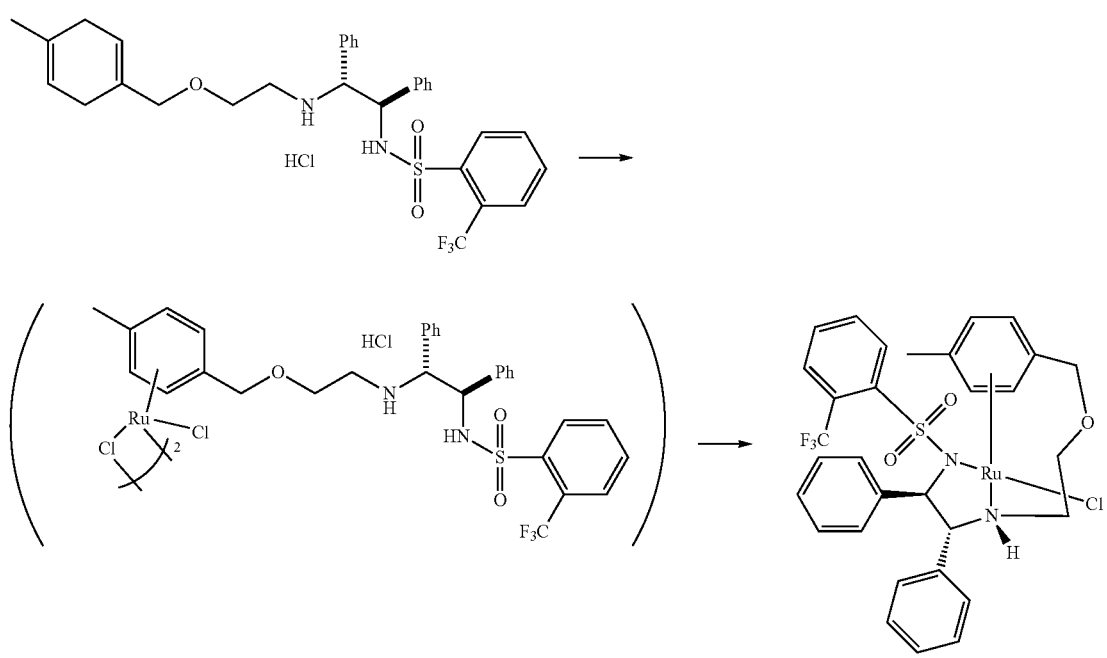

5.0 g (8.25 mmol) of the diamine hydrochloride produced in Example 42 was dissolved in 66 ml of 3-methoxypropanol and 22 ml of water. 1.79 g (6.86 mmol) of ruthenium trichloride trihydrate and 0.58 g (6.86 mmol) of sodium hydrogen carbonate were added to the solution, and the resulting mixture was stirred for 2 hours at 120° C. 50 ml of 3-methoxypropanol was recovered, and then 75 ml of MIBK and 2.78 g (27.45 mmol) of triethylamine were added to the residue. The mixture was stirred for one hour at 60° C. 0.3 M hydrochloric acid was added thereto, and the organic layer was separated. The obtained organic layer was washed two times with water. After washing, about 60 ml of the solvent was recovered, and 85 ml of heptane was added to the residue. The mixture was subjected to crystallization. Crystals precipitated therefrom were collected by filtration, and thus 4.60 g of the desired Ru complex was obtained. Yield 95.2%.

$^1$H-NMR(CD$_2$Cl$_2$, 300 MHz) δ:

2.50 (s, 3H), 3.15-3.20 (m, 1H), 3.70-3.82 (m, 2H), 4.00 (m, 2H), 4.15 (m, 1H), 4.40 (m, 1H), 4.80 (m, 1H), 5.10 (d, 1H), 5.45 (d, 1H), 5.62 (d, 1H), 5.70 (d, 1H), 6.38 (d, 1H), 6.50-7.50 (m, 14H);

$^{19}$F-NMR(DMSO-d$_6$) δ:

−58.45

HRMS (ESI) As C$_{31}$H$_{30}$CN$_2$O$_3$F$_3$RuS.

Calculated value: [M+H]$^+$ 705.7034.

Found value: 705.0758.

Example 44

Asymmetrichydrogen Transfer Reaction of Acetophenone Using Complex RuCl((R,R)—O-HT-o-TFTsdpen) (S/C=1000)

In a 50-ml Schlenk tube, 3.5 mg (0.005 mmol) of the complex RuCl((R,R)—O-HT-o-TFTsdpen) produced in Example 43 as described above, 0.58 ml (0.60 g, 5 mmol) of acetophenone, and 2.5 ml of a formic acid-triethylamine (5:2) azeotropic mixture were mixed, and the Schlenk tube was purged with nitrogen. Subsequently, the mixture was allowed to react for 5 hours at 60° C. An analysis of the reaction liquid was carried out by GC, and it was found that (R)-1-phenylethanol with 97.5% ee was produced at a conversion rate of 98.9%.

Example 45

Production of 2,4,6-triisopropyl-N-((1S,2S)-2-(2-((4-methylcyclohexa-1,4-dienyl)methoxy)ethylamino)-1,2-diphenylethyl)benzenesulfonamide

[Chem. 30]

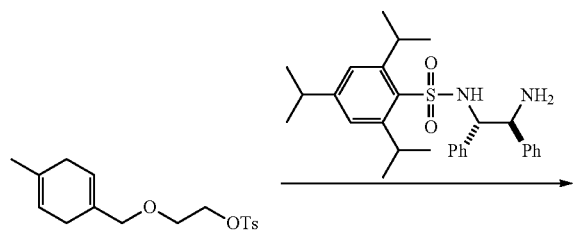

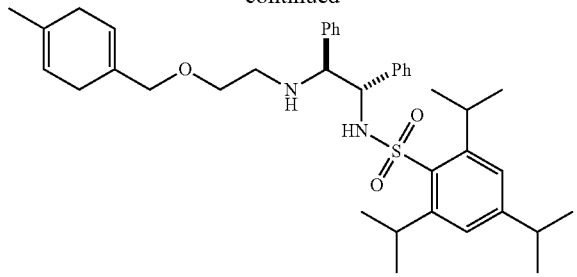

6.03 g (18.82 mmol) of the tosylate obtained in Example 37 as described above was dissolved in 25 ml of toluene, and 2.43 g (18.82 mmol) of DIPEA and 9.00 g (18.80 mmol) of (S,S)-TIPPsDPEN were added to the solution. The mixture was stirred for 13 hours at 135° C. Subsequently, the solvent was distilled off under reduced pressure, and the residue thus obtained was purified by silica gel column chromatography (toluene/ethyl acetate=20/1→15/1). Thus, 10.53 g of the title compound was obtained as a colorless oil. Yield 89.0%.

$^1$H-NMR(CDCl$_3$, 300 MHz) δ:

1.06 (d, J=6.9 Hz, 3H), 1.21 (d, J=6.9 Hz, 3H), 1.87 (brs, 1H), 1.68 (s, 3H), 2.60 (brs, 4H), 2.71-2.48 (m, 2H), 3.52-3.34 (m, 2H), 3.55 (d, J=8.9 Hz, 1H), 3.77 (s, 2H), 3.95 (septet, J=6.7 Hz, 3H), 4.40 (d, J=8.9 Hz, 1H), 5.44 (m, 1H), 5.64 (m, 1H), 6.52 (brs, 1H), 6.74-7.28 (m, 12H);

HRMS (ESI):

As C$_{39}$H$_{53}$N$_2$O$_3$S.

Calculated value: [M+H]$^+$ 629.3771.

Found value: 629.3771.

Example 46

Production of RuCl((S,S)—O-HT-TIPPsdpen)

[Chem. 31]

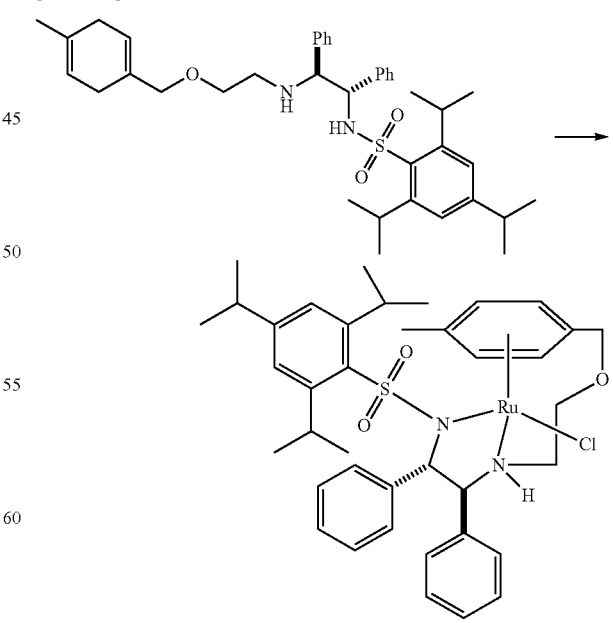

2.02 g (3.21 mmol) of the sulfonamide obtained in Example 45 as described above was dissolved in 8 ml of methanol. Under ice cooling, 0.67 g (6.42 mmol) of a 1 M methanol solution of hydrochloric acid was added to the solution, and the mixture was stirred for 20 minutes at room temperature. Subsequently, the solvent was distilled off under reduced pressure, and the residue thus obtained was dissolved in 30 ml of 3-methoxypropanol and 18 ml of water. 0.72 g (2.75 mmol) of ruthenium trichloride trihydrate was added to the solution, and the mixture was stirred for one hour at 120° C. The solvent was distilled off under reduced pressure, and to the residue thus obtained, 35 ml of IPA and 0.72 g (7.15 mmol) of triethylamine were added. The resulting mixture was stirred for one hour at 60° C. The solvent was distilled off under reduced pressure, and the residue thus obtained was purified by silica gel column chromatography (chloroform/methanol=97/3→20/1). Thus, 1.28 g of the desired Ru complex was obtained. Yield 52.3%.

$^1$H-NMR(CD$_2$Cl$_2$ 500 MHz) δ:
1.0-1.2 (m, 18H), 1.70 (m, 1H), 2.41 (s, 3H), 2.60 (m, 1H), 3.05 (m, 1H), 3.35 (m, 1H), 3.68 (m, 1H), 3.75 (t, 1H), 3.85 (m, 2H), 4.18 (d, 1H), 4.25 (d, 1H), 4.85 (brs, 1H), 5.02 (d, 1H), 5.30 (d, 1H), 5.48 (d, 1H), 5.63 (d, 1H), 6.35 (d, 1H), 6.40-6.70 (m, 10H), 6.90-7.05 (m, 3H);
HRMS (ESI):
As C$_{39}$H$_{50}$N$_2$O$_3$SClRu.
Calculated value: [M+H]$^+$ 763.2269.
Found value: 763.2257.

Example 47

Asymmetric Hydrogen Transfer Reaction of Acetophenone Using Complex RuCl((S,S)—O-HT-TIPPsdpen) (S/C=1000)

In a 50-ml Schlenk tube, 2.8 mg (0.005 mmol) of the complex RuCl(S,S)—O-HT-TIPPsDPEN) produced in Example 46 as described above, 0.58 ml (0.60 g, 5 mmol) of acetophenone, and 2.5 ml of a formic acid-triethylamine (5:2) azeotropic mixture were mixed, and the Schlenk tube was purged with nitrogen. Subsequently, the mixture was allowed to react for 10 hours at 60° C. An analysis of the reaction liquid was carried out by GC, and it was found that (S)-1-phenylethanol with 95.8% ee was produced at a conversion rate of 38.5%.

Example 48

Production of 4-(4,5-dimethylcyclohexa-1,4-dienyl)butan-1-ol

[Chem. 32]

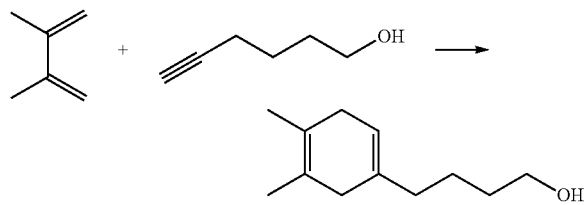

800 mg (2.00 mmol) of 1,2-bis(diphenylphosphino)ethane, 437 mg (2.00 mmol) of cobalt bromide, 1.28 g (4.00 mmol) of zinc iodide, and 260 mg (4.00 mmol) of zinc were added to 40 ml of THF, and the solution was stirred for 15 minutes at 70° C. The solution was cooled to room temperature, and 9.86 g (120 mmol) of 2,3-dimethyl-1,3-butadiene was added thereto. Subsequently, 9.8 g (100 mmol) of 5-hexyn-1-ol was slowly added dropwise to the mixture in a water bath. The resulting mixture was stirred for one hour at 35° C., and then the solvent was distilled off under reduced pressure. The residue thus obtained was purified by silica gel column chromatography (hexane/ethyl acetate=3/1), and thus 11.5 g of the title compound alcohol was obtained as a colorless oil. Yield 63.4%.

$^1$H-NMR(CDCl$_3$, 300 MHz) δ:
1.28 (bs, 1H), 1.79-1.46 (m, 4H), 1.63 (s, 6H), 1.98-2.11 (m, 3H), 2.48-2.61 (m, 2H), 3.63-3.67 (m, 2H), 5.41-5.56 (m, 1H);

Example 49

Production of 4-(4,5-dimethylcyclohexa-1,4-dienyl)butyl 4-methylbenzenesulfonate

[Chem. 33]

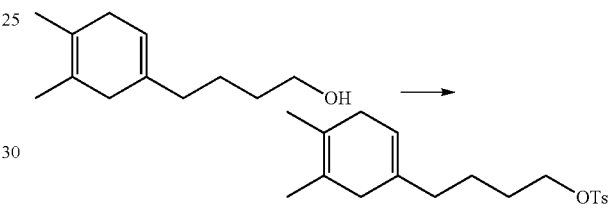

11.0 g (61.0 mmol) of 4-(4,5-dimethylcyclo-1,4-diene)butan-1-ol, 7.40 g (73.08 mmol) of triethylamine, and 6.0 g (73.0 mmol) of 1-methylimidazole were dissolved in 55 ml of toluene. In an ice bath, 40 ml of a toluene solution of 13.9 g (73.1 mmol) of p-toluenesulfonyl chloride was slowly added dropwise to the solution, and then the resulting mixture was stirred for one hour at room temperature. Water was added to the mixture, and the organic layer was separated. The obtained organic layer was washed with 2 M hydrochloric acid and water. The solvent was distilled off under reduced pressure, and the residue thus obtained was purified by silica gel column chromatography (hexane/ethyl acetate=20/1→4/1). Thus, 16.3 g of tosylate of the title compound was obtained. Yield 80%.

$^1$H-NMR(CDCl$_3$, 300 MHz) δ:
1.60-1.41 (m, 2H), 1.67 (s, 6H), 1.79-1.74 (m, 3H), 1.89-2.05 (m, 3H), 2.45 (s, 3H), 2.53 (brs, 2H), 4.00-4.05 (m, 2H), 5.28-5.40 (m, 1H), 7.33-7.36 (d, 2H), 7.77-7.80 (d, 2H);

Example 50

Production of N-((1R,2R)-2-(2-((4,5-dimethylcyclohexa-1,4-dienyl)methoxy)ethylamino)-1,2-diphenyl-ethyl)methanesulfonamide

[Chem. 34]

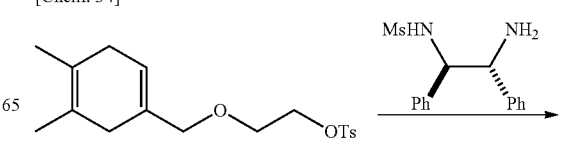

51
-continued

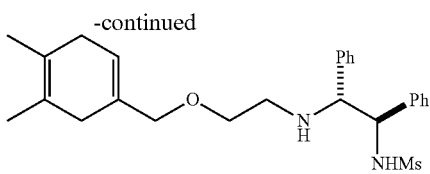

8.00 g (23.78 mmol) of the tosylate obtained in Example 49 was dissolved in 35 ml of toluene, and 3.07 g (23.78 mmol) of DIPEA and 6.90 g (23.78 mmol) of (R,R)-MsDPEN were added to the solution. The mixture was stirred for 12.5 hours at 135° C. Subsequently, the solvent was distilled off under reduced pressure, and the residue thus obtained was purified by silica gel column chromatography (hexane/ethyl acetate=2/1). Thus, 9.83 g of the title compound was obtained as a colorless solid. Yield 90.9%.

$^1$H-NMR(CDCl$_3$, 300 MHz) δ:
1.65 (s, 3H), 1.68 (s, 3H), 1.89-1.75 (m, 1H), 2.33 (s, 3H), 2.46-2.54 (m, 3H), 2.60-2.71 (m, 3H), 3.35-3.48 (m, 2H), 3.77 (s, 2H), 3.81 (d, J=7.8 Hz, 1H), 4.47 (d, J=7.8 Hz, 1H), 5.60 (m, 1H), 6.21 (brs, 1H), 7.10-7.27 (m, 10H);
HRMS (ESI):
As C$_{26}$H$_{35}$N$_2$O$_3$S.
Calculated value: [M+H]$^+$ 455.2363.
Found value: 455.2358.

Example 51

Production of RuCl(R,R)-xyl-O-HT-Msdpen)

[Chem. 35]

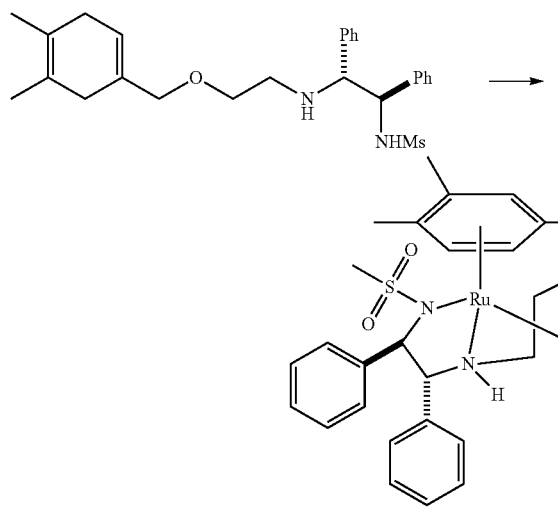

2.00 g (4.40 mmol) of the diamine compound obtained in Example 50 was dissolved in 8 ml of dichloromethane. Under ice cooling, 0.92 g (8.80 mmol) of a 1 M methanol solution of hydrochloric acid was added to the solution, and the mixture was stirred for 20 minutes at room temperature. Subsequently, the solvent was distilled off under reduced pressure, and the residue thus obtained was dissolved in 30 ml of 3-methoxypropanol and 18 ml of water. 0.97 g (3.71 mmol) of ruthenium trichloride trihydrate was added to the solution, and the resulting mixture was stirred for one hour at 120° C. The solvent was distilled off under reduced pressure, and to the residue thus obtained, 35 ml of IPA and 0.80 g (7.87 mmol) of triethylamine were added. The resulting mixture was stirred for one hour at 60° C. The solvent was distilled off under reduced pressure, and the residue thus obtained was purified by silica gel column chromatography (chloroform/methanol=97/3→20/1). Thus, 1.48 g of the desired Ru complex was obtained. Yield 57.2%.

$^1$H-NMR(CDCl$_3$, 300 MHz) δ:
2.27 (s, 3H), 2.30 (s, 3H), 2.39 (s, 3H), 3.15-3.35 (m, 2H), 3.75-3.85 (m, 2H), 4.00-4.10 (m, 2H), 3.95-4.05 (brs, 1H), 4.42 (d, 1H), 4.85 (d, 1H), 5.50 (d, 1H), 5.76 (s, 1H), 5.85 (d, 1H), 6.82-7.22 (m, 10H);
HRMS (ESI):
As C$_{26}$H$_{32}$N$_2$O$_3$SClRu.
Calculated value: [M+H]$^+$ 589.0860.
Found value: 589.0863.

Example 52

Asymmetric Hydrogen Transfer Reaction of Acetophenone Using Complex RuCl(R,R)-xyl-O-HT-Msdpen) (S/C=1000)

In a 50-ml Schlenk tube, 2.8 mg (0.005 mmol) of the complex RuCl((R,R)-xyl-O-HT-Msdpen) produced in Example 51 as described above, 0.58 ml (0.60 g, 5 mmol) of acetophenone, and 2.5 ml of a formic acid-triethylamine (5:2) azeotropic mixture were mixed, and the Schlenk tube was purged with nitrogen. Subsequently, the mixture was reacted for 10 hours at 60° C. An analysis of the reaction liquid was carried out by GC, and it was found that (R)-1-phenylethanol with 95.9% ee was produced at a conversion rate of 95.4%.

Example 53

Production of 4-methyl-N-((1R,2R)-2-(2-((4-methyl-cyclohexa-1,4-dienyl)methoxy)ethylamino)cyclohexyl)benzenesulfonamide hydrochloride

[Chem. 36]

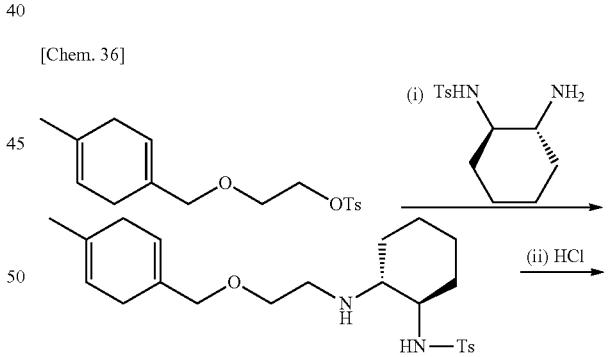

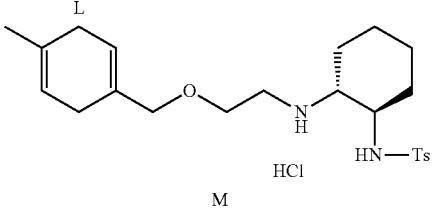

5.06 g (16.4 mmol) of the tosylate obtained in Example 37 was dissolved in 26 ml of toluene, and 2.12 g (16.4 mmol) of DIPEA, 4.00 g (14.9 mmol) of (R,R)-TsCYDN, and 2.72 g (16.4 mmol) of potassium iodide were added to the solution.

The resulting mixture was stirred for 20 hours at 135° C. The reaction liquid was concentrated and purified by silica gel column chromatography. Thereby, 2.92 g of diamine L was obtained. Yield 46.9%. Subsequently, 42 ml of dichloromethane and 24.6 ml of an HCl-methanol solution (1 N) were added to 2.8 g (6.69 mmol) of the diamine L, and the resulting mixture was stirred for 0.5 hours. Subsequently, the solvent was removed, and thus 2.9 g of the desired diamine hydrochloride M was obtained. Yield 94.7%.

$^1$H-NMR(DMSO-d$_6$, 300 MHz) δ:

0.95-1.30 (m, 4H), 1.50 (m, 2H), 1.63 (s, 3H), 2.10 (m, 2H), 2.40 (s, 3H), 2.60 (m, 2H), 2.95 (brd, 1H), 3.18 (m, 2H), 3.60 (m, 2H), 3.90 (s, 2H), 5.40 (m, 1H), 5.70 (m, 1H), 7.40 (d, 1H), 7.75 (d, 1H), 8.15 (d, 1H), 8.23 (brd, 1H), 9.10 (brd, 1H)

HRMS (ESI):

As $C_{23}H_{34}N_2O_3S$.

Calculated value: $[M-Cl]^+$ 419.2363.

Found value: 419.2365.

Example 54

Production of RuCl(R,R)—O-HT-Tscydn)

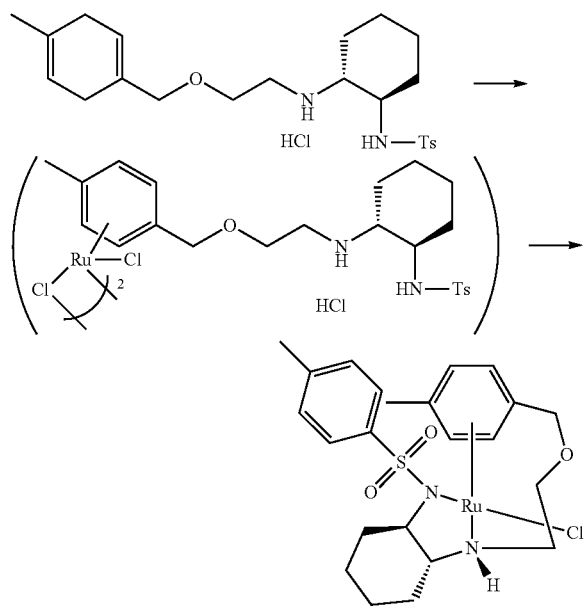

0.5 g (1.1 mmol) of the diamine hydrochloride produced in Example 53 was dissolved in 15 ml of 3-methoxypropanol and 3 ml of water. 0.25 g (0.96 mmol) of ruthenium trichloride trihydrate and 0.08 g (0.96 mmol) of sodium hydrogen carbonate were added to the solution, and the resulting mixture was stirred for one hour at 120° C. 12 ml of 3-methoxypropanol was recovered, and then 13 ml of MIBK and 0.39 g (3.82 mmol) of triethylamine were added to the residue. The resulting mixture was stirred for one hour at 60° C. 0.3 M hydrochloric acid was added thereto, and the organic layer was separated. The obtained organic layer was washed two times with water. After washing, approximately 10 ml of the solvent was recovered, 15 ml of heptane was added to the residue, and the resulting mixture was subjected to crystallization. Crystals precipitated therefrom were collected by filtration, and thus 0.24 g of the desired Ru complex was obtained. Yield 45.5%.

$^1$H-NMR(CD$_2$Cl, 500 MHz) δ:

0.65-1.05 (m, 4H), 1.90 (m, 1H), 1.15 (m, 1H), 2.08 (m, 1H), 2.70 (m, 1H), 2.75 (s, 1H), 2.77 (s, 1H), 2.60 (m, 1H), 3.60-3.70 (m, 2H), 3.80 (m, 1H), 4.00 (m, 1H), 4.25 (m, 1H), 4.35 (d, 1H), 4.92 (d, 1H), 5.25 (d, 1H), 5.50 (d, 1H), 5.67 (d, 1H), 5.83 (d, 1H), 7.20 (d, 1H), 7.80 (d, 1H);

HRMS (ESI):

As $C_{23}H_{31}N_2O_3RuS$.

Calculated value: $[M-Cl]^+$ 517.1093.

Found value: 517.1101.

Example 55

Asymmetric Hydrogen Transfer Reaction of Acetophenone Using Complex RuCl(R,R)—O-HT-Tscydn) (S/C=1000)

In a 50-ml Schlenk tube, 2.8 mg (0.005 mmol) of the complex RuCl(R,R)—O-HT-Tscydn) produced in Example 54 as described above, 0.58 ml (0.60 g, 5 mmol) of acetophenone, and 2.5 ml of a formic acid-triethylamine (5:2) azeotropic mixture were mixed, and the Schlenk tube was purged with nitrogen. Subsequently, the mixture was allowed to react for 10 hours at 60° C. An analysis of the reaction liquid was carried out by GC, and it was found that (R)-1-phenylethanol with 95.5% ee was produced at a conversion rate of 73.7%.

Example 56

Production of 2,4,6-trimethyl-N-((1R,2R)-2-(2-(4-methylcyclohexa-1,4-dienyl)methoxy)ethylamino)-1,2-diphenylethyl)benzenesulfonamide

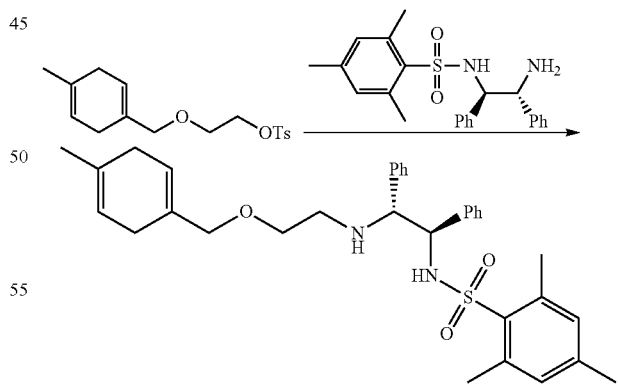

1.0 g (3.0 mmol) of the tosylate obtained in Example 37 was dissolved in 5 ml of toluene, and 0.39 g (3.0 mmol) of DIPEA and 1.3 g (3.3 mmol) of (R,R)-MESsDPEN were added to the solution. The mixture was stirred for 8 hours at 120° C. Subsequently, the solvent was distilled off under reduced pressure, and the residue thus obtained was purified by silica gel column chromatography (toluene/ethyl acetate=4/1). Thus, 0.71 g of the title compound was obtained as a colorless oil. Yield 44.7%.

Example 57

Production of RuCl(R,R)—O-HT-MESsDPEN)

[Chem. 39]

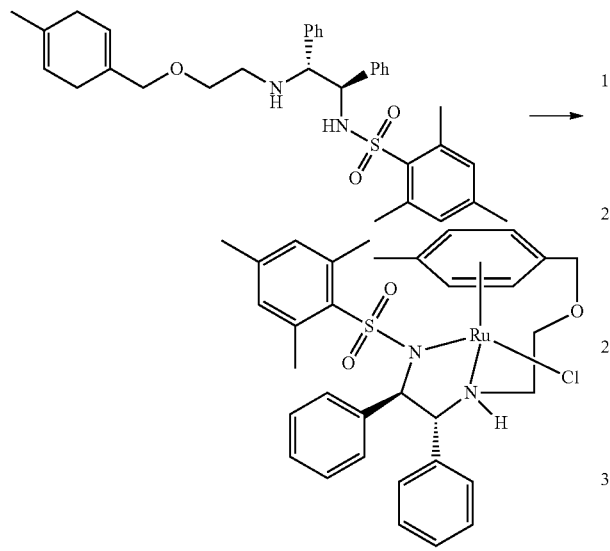

0.67 g (1.2 mmol) of the sulfonamide obtained in Example 56 was dissolved in 5 ml of methanol. Under ice cooling, 0.25 g (2.4 mmol) of a 1 M methanol solution of hydrochloric acid was added to the solution, and the resulting mixture was stirred for 20 minutes at room temperature. Subsequently, the solvent was distilled off under reduced pressure, and the residue thus obtained was dissolved in 20 ml of 2-methoxyethanol, 2 ml of water, and 0.09 g (1.2 mmol) of sodium hydrogen carbonate. 0.36 g (1.35 mmol) of ruthenium trichloride trihydrate was added to the solution, and the resulting mixture was stirred for 3 hours at 120° C. The solvent was distilled off under reduced pressure, and to the residue thus obtained, 40 ml of ethanol and 0.5 g (4.94 mmol) of triethylamine were added. The resulting mixture was stirred for 2 hours at 80° C. The solvent was distilled off under reduced pressure, and the residue thus obtained was purified by silica gel column chromatography (chloroform/methanol=20/1). Thus, 0.13 g of the desired Ru complex was obtained. Yield 16.0%.

$^1$H-NMR(CD$_2$Cl, 500 MHz) δ:

1.95 (s, 3H), 2.45 (s, 6H), 2.46 (s, 3H), 3.05 (m, 1H), 3.70 (m, 1H), 3.80 (d, 1H), 3.85 (m, 2H), 3.95 (d, 1H), 4.25 (d, 1H), 4.75 (m, 1H), 5.00 (d, 1H), 5.40 (d, 1H), 5.50 (d, 1H), 5.60 (d, 1H), 6.30 (s, 2H), 6.53 (d, 1H), 6.40-7.00 (m, 10H);

HRMS (ESI):

As C$_{33}$H$_{37}$ClN$_2$O$_3$RuS.

Calculated value: [M+H]$^+$ 679.1335.

Found value: 679.1327.

Example 58

Production of Ru((R,R)—O-HT-TsDPEN)

[Chem. 40]

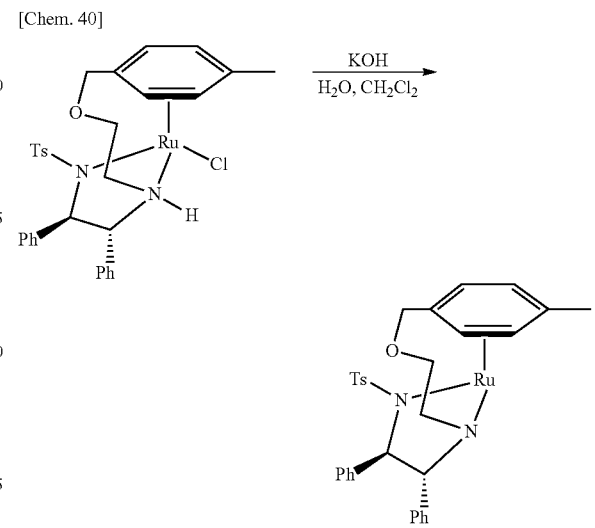

To a suspension of RuCl(R,R)—O-HT-TsDPEN) 140 mg (0.215 mmol) and potassium hydroxide 84 mg (1.28 mmol) in dichloromethane (10 mL) was added water (1 mL). The reaction mixture was stirred at room temperature for 20 min. Then the organic solution was washed with water three times (10 mL×3). The organic layer was concentrated under reduced pressure to give the desired product as purple solid. Yield 125 mg (95%)

$^1$H NMR (500 MHz, CD$_2$Cl$_2$) δ 7.48 (d, J=7.3 Hz, 2H), 7.40 (d, J=8.0 Hz, 2H), 7.30-6.85 (m, 8H), 6.98 (d, J=8.0 Hz, 2H), 6.15 (d, J=6.3 Hz, 1H), 5.55 (d, J=6.0 Hz, 1H), 5.45 (dd, J=6.3, 6.0 Hz, 2H), 4.95 (d, J=14.4 Hz, 1H), 4.35 (d, J=14.4 Hz, 1H), 4.13 (s, 1H), 3.55-3.42 (m, 2H), 3.36-3.28 (m, 1H), 3.35 (s, 1H), 3.08-3.00 (m, 1H), 2.60 (s, 3H), 2.32 (s, 3H);

HRMS (ESI):

As C$_{31}$H$_{33}$N$_2$O$_3$S.

Calculated value: [M+H]$^+$ 615.1250.

Found value: 615.1231.

Example 59

Production of RuH((R,R)—O-HT-TsDPEN)

[Chem. 41]

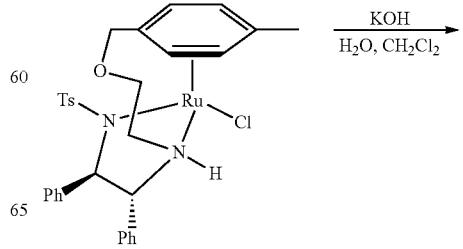

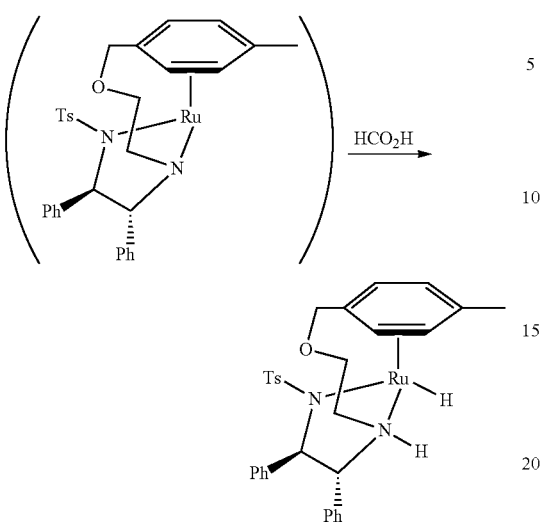

To a suspension of RuCl(R,R)—O-HT-TsDPEN) 140 mg (0.215 mmol) and potassium hydroxide 84 mg (1.28 mmol) in dichloromethane (10 mL) was added water (1 mL). The reaction mixture was stirred at room temperature for 20 min. Then the organic solution was washed with water three times (10 mL×3). The organic layer was separated to another Schlenk tube and this solution was added formic acid (2 mL). The reaction mixture was stirred at room temperature for 5 min. Then the organic solution was washed with water three times (10 mL×3). The organic layer was concentrated under reduced pressure to give the desired product as light brown solid. Yield 120 mg (90%)

$^{1}$H NMR (300 MHz, CD$_2$Cl$_2$) 67 7.50-6.60 (m, 14H), 6.30 (d, J=4.5 Hz, 1H), 6.05 (m, 2H), 5.45 (m, 1H), 4.85 (d, J=13.5 Hz, 1H), 4.78 (d, J=4.5 Hz, 1H), 4.25-3.90 (m, 4H), 3.85 (d, J=13.5 Hz, 1H), 3.20-3.15 (m, 1H), 2.80-2.70 (m, 1H), 2.22 (s, 3H), 2.20 (s, 1H), −5.10 (s, 1H);

HRMS (ESI):

As C$_{31}$H$_{33}$N$_2$O$_3$S Calculated value: [M−H]$^+$ 615.1250.

Found value: 615.1243.

Example 60

Production of Ru (BF$_4$)((R,R)—O-HT-TsDPEN)

[Chem. 42]

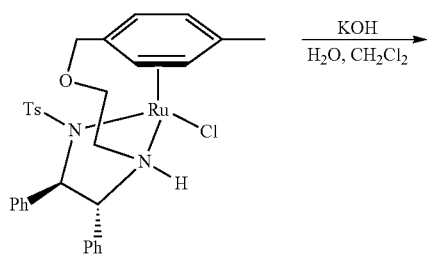

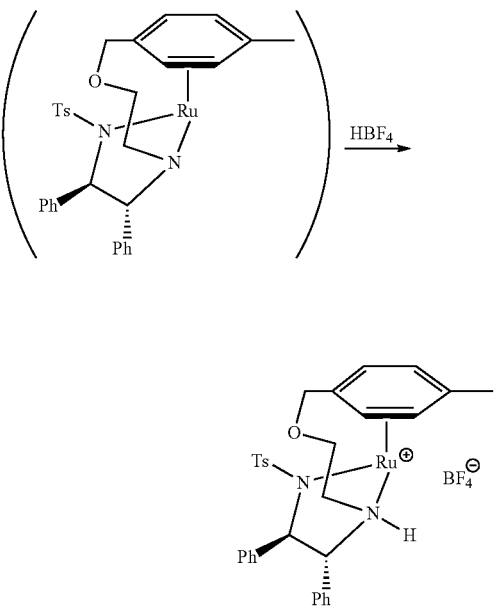

To a suspension of RuCl(R,R)—O-HT-TsDPEN) 140 mg (0.215 mmol) and potassium hydroxide 84 mg (1.28 mmol) in dichloromethane (10 mL) was added water (1 mL). The reaction mixture was stirred at room temperature for 20 min. Then the organic solution was washed with water three times (10 mL×3). The organic layer was separated to another Schlenk tube and this solution was added 42% aqueous HBF$_4$ solution (0.5 mL). The reaction mixture was stirred at room temperature for 5 min. Then the organic solution was washed with water three times (10 mL×3). The organic layer was concentrated under reduced pressure to give the desired product as brown solid. Yield 136 mg (90%)

$^{1}$H-NMR(CD$_3$OD, 300 MHz) δ:

2.12 (s, 3H), 2.46 (s, 3H), 3.35-3.60 (m, 4H), 3.60-3.80 (m, 1H), 3.95-4.10 (m, 3H), 4.70-4.80 (m, 1H), 5.84 (d, 1H), 5.89 (d, 1H), 5.99 (d, 1H), 6.20 (d, 1H), 6.46-7.50 (m, 14H)

HRMS (ESI):

As C$_{31}$H$_{33}$BF$_4$N$_2$O$_3$RuS.

Calculated value: [M−BF$_4$]$^+$ 615.1250.

Found value: 615.1271.

INDUSTRIAL APPLICABILITY

The present invention provides a novel ruthenium complex which can be produced conveniently and safely. The ruthenium complex of the present invention is a ruthenium complex which has a very strong catalytic activity, is useful as a catalyst for various hydrogenation reactions, is also useful as a catalyst for asymmetric reduction having excellent stereoselectivity and capable of giving a high enantiomeric excess, and is useful in the field of industrial chemistry.

The invention claimed is:
1. A ruthenium complex represented by the following formula (1):

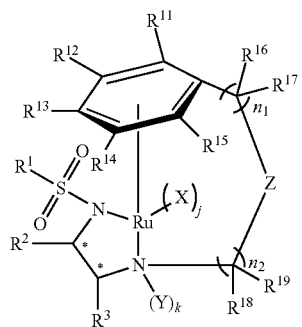

(1)

wherein symbol * represents an asymmetric carbon atom;
$R^1$ represents an alkyl group having 1 to 10 carbon atoms; a halogenated alkyl group having 1 to 10 carbon atoms; 10-camphoryl group; an amino group which is optionally substituted with one or two alkyl group having 1 to 10 carbon atoms; an aryl group which is optionally substituted with an alkyl group having 1 to 10 carbon atoms, a halogenated alkyl group having 1 to 10 carbon atoms, a halogen atom, a cyano group (—CN), an amino group, an alkylated amino group (—$NR^{20}R^{21}$), a five or six membered cyclic amino group, an acylated amino group (—NH—CO—$R^{20}$), a hydroxyl group, an alkoxy group (—$OR^{20}$), an acyl group (—CO—$R^{20}$), a carboxyl group, an alkoxycarbonyl group (—$COOR^{20}$), a phenoxy carbonyl group, a mercapto group, an alkylthio group (—$SR^{20}$), a silyl group (—$SiR^{20}R^{21}R^{22}$), or a nitro group (—$NO_2$); $R^{20}$, $R^{21}$ and $R^{22}$ each independently represent a hydrogen atom, an alkyl group having 1 to 10 carbon atoms or a cycloalkyl group having 3 to 10 carbon atoms;
Y represents a hydrogen atom;
X represents a trifluoromethanesulfonyloxy group, a p-toluenesulfonyloxy group, a methanesulfonyloxy group, a benzenesulfonyloxy group, a hydrogen atom, or a halogen atom;
j and k each represent 0 or 1, but j+k is not 1;
$R^2$ and $R^3$ each independently represent a hydrogen atom; an alkyl group having 1 to 10 carbon atoms; a phenyl group which is optionally substituted with an alkyl group having 1 to 10 carbon atoms, an alkoxy group having 1 to 10 carbon atoms, or a halogen atom; or a cycloalkyl group having 3 to 8 carbon atoms, or $R^2$ and $R^3$ is optionally joined together to form a ring;
$R^{11}$, $R^{12}$, $R^{13}$, $R^{14}$ and $R^{15}$ each independently represent a hydrogen atom, an alkyl group having 1 to 10 carbon atoms, or an alkoxy group having 1 to 10 carbon atoms;
$R^{16}$ and $R^{17}$ each independently represent a hydrogen atom, a hydroxyl group, an alkyl group having 1 to 10 carbon atoms, or an alkoxy group having 1 to 10 carbon atoms, or one $R^{16}$ and one $R^{17}$ with the carbon atom which is substituted with said one $R^{16}$ and one $R^{17}$ form a carbonyl group;
$R^{18}$ and $R^{19}$ each independently represent a hydrogen atom, a hydroxyl group, an alkyl group having 1 to 10 carbon atoms, or an alkoxy group having 1 to 10 carbon atoms, or one $R^{18}$ and one $R^{19}$ with the carbon atom which is substituted with said one $R^{18}$ and one $R^{19}$ form a carbonyl group;

Z represents an oxygen atom or a sulfur atom; and
$n_1$ represents 1 or 2, and $n_2$ represents 1, 2 or 3.

2. A method for producing a reduction product by reducing an organic compound in the presence of the ruthenium complex as set forth in claim 1 and a hydrogen donor.

3. The method according to claim 2, wherein the hydrogen donor is selected from formic acid, a formic acid alkali metal salt, and an alcohol having a hydrogen atom on the α-position carbon atom substituted with a hydroxyl group.

4. The method according to claim 2, wherein the hydrogen donor is hydrogen.

5. A method for producing an optically active alcohol, the method comprising reducing a carbonyl group of a carbonyl compound in the presence of the ruthenium complex according to claim 1 and a hydrogen donor.

6. A method for producing an optically active amine, the method comprising reducing an imino group of an imine compound in the presence of the ruthenium complex according to claim 1 and a hydrogen donor.

7. A catalyst for reduction, comprising the ruthenium complex according to claim 1.

8. The catalyst according to claim 7, wherein the catalyst is a catalyst for asymmetric reduction.

9. A ruthenium complex represented by the following formula (2):

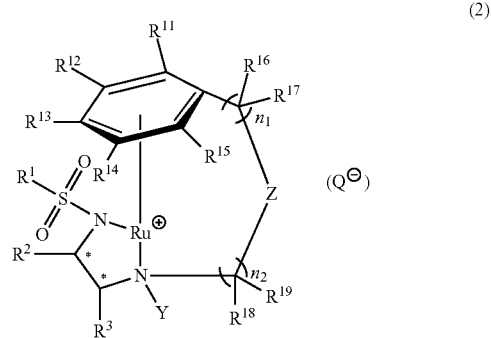

(2)

wherein symbol * represents an asymmetric carbon atom;
$R^1$ represents an alkyl group having 1 to 10 carbon atoms; a halogenated alkyl group having 1 to 10 carbon atoms; 10-camphoryl group; an amino group which is optionally substituted with one or two alkyl group having 1 to 10 carbon atoms; an aryl group which is optionally substituted with an alkyl group having 1 to 10 carbon atoms, a halogenated alkyl group having 1 to 10 carbon atoms, a halogen atom, a cyano group (—CN), an amino group, an alkylated amino group (—$NR^{20}R^{21}$), a five or six membered cyclic amino group, an acylated amino group (—NH—CO—$R^{20}$), a hydroxyl group, an alkoxy group (—$OR^{23}$), an acyl group (—CO—$R^{20}$), a carboxyl group, an alkoxycarbonyl group (—$COOR^{20}$), a phenoxy carbonyl group, a mercapto group, an alkylthio group (—$SR^{20}$), a silyl group (—$SiR^{20}R^{21}R^{22}$), or a nitro group (—$NO_2$); $R^{20}$, $R^{21}$ and $R^{22}$ each independently represent a hydrogen atom, an alkyl group having 1 to 10 carbon atoms or a cycloalkyl group having 3 to 10 carbon atoms;
Y represents a hydrogen atom;
$R^2$ and $R^3$ each independently represent a hydrogen atom; an alkyl group having 1 to 10 carbon atoms; a phenyl group which is optionally substituted with an alkyl group having 1 to 10 carbon atoms, an alkoxy group having 1 to 10 carbon atoms, or a halogen atom; or a cycloalkyl group having 3 to 8 carbon atoms, or $R^2$ and $R^3$ is optionally joined together to form a ring;

$R^{11}$, $R^{12}$, $R^{13}$, $R^{14}$ and $R^{15}$ each independently represent a hydrogen atom, an alkyl group having 1 to 10 carbon atoms, or an alkoxy group having 1 to 10 carbon atoms;

$R^{16}$ and $R^{17}$ each independently represent a hydrogen atom, a hydroxyl group, an alkyl group having 1 to 10 carbon atoms, or an alkoxy group having 1 to 10 carbon atoms, or one $R^{16}$ and one $R^{17}$ with the carbon atom which is substituted with said one $R^{16}$ and one $R^{17}$ form a carbonyl group;

$R^{18}$ and $R^{19}$ each independently represent a hydrogen atom, a hydroxyl group, an alkyl group having 1 to 10 carbon atoms, or an alkoxy group having 1 to 10 carbon atoms, or one $R^{18}$ and one $R^{19}$ with the carbon atom which is substituted with said one $R^{18}$ and one $R^{19}$ form a carbonyl group;

Z represents an oxygen atom or a sulfur atom;

$Q^-$ represents a counter anion; and $n_1$ represents 1 or 2, and $n_2$ represents 1, 2 or 3.

10. A method for producing a reduction product by reducing an organic compound in the presence of the ruthenium complex as set forth in claim 9 and a hydrogen donor.

11. The method according to claim 10, wherein the hydrogen donor is selected from formic acid, a formic acid alkali metal salt, and an alcohol having a hydrogen atom on the α-position carbon atom substituted with a hydroxyl group.

12. The method according to claim 10, wherein the hydrogen donor is hydrogen.

13. A method for producing an optically active alcohol, the method comprising reducing a carbonyl group of a carbonyl compound in the presence of the ruthenium complex according to claim 9 and a hydrogen donor.

14. A method for producing an optically active amine, the method comprising reducing an imino group of an imine compound in the presence of the ruthenium complex according to claim 9 and a hydrogen donor.

15. A catalyst for reduction, comprising the ruthenium complex according to claim 9.

16. The catalyst according to claim 15, wherein the catalyst is a catalyst for asymmetric reduction.

* * * * *